United States Patent
Ochs et al.

(10) Patent No.: US 10,537,289 B2
(45) Date of Patent: *Jan. 21, 2020

(54) SYSTEMS AND METHODS FOR FILTERING AUTOCORRELATION PEAKS AND DETECTING HARMONICS

(71) Applicant: Covidien LP, Mansfield, MA (US)

(72) Inventors: James Ochs, Palo Alto, CA (US); Scott McGonigle, Edinburgh (GB); Paul Addison, Edinburgh (GB)

(73) Assignee: COVIDIEN LP, Mansfield, MA (US)

(*) Notice: Subject to any disclaimer, the term of this patent is extended or adjusted under 35 U.S.C. 154(b) by 6 days.

This patent is subject to a terminal disclaimer.

(21) Appl. No.: 15/903,821

(22) Filed: Feb. 23, 2018

(65) Prior Publication Data

US 2018/0177460 A1    Jun. 28, 2018

Related U.S. Application Data

(63) Continuation of application No. 14/628,004, filed on Feb. 20, 2015, now Pat. No. 9,901,308.

(Continued)

(51) Int. Cl.
*A61B 5/00* (2006.01)
*A61B 5/08* (2006.01)
(Continued)

(52) U.S. Cl.
CPC ........ *A61B 5/7246* (2013.01); *A61B 5/02416* (2013.01); *A61B 5/0816* (2013.01);
(Continued)

(58) Field of Classification Search
CPC .............. A61B 5/02416; A61B 5/0816; A61B 5/14551; A61B 5/7203; A61B 5/7246; A61B 5/7278
(Continued)

(56) References Cited

U.S. PATENT DOCUMENTS

| 5,188,108 A | 2/1993 | Secker |
| 5,285,783 A | 2/1994 | Secker |

(Continued)

FOREIGN PATENT DOCUMENTS

| EP | 0072601 | 2/1983 |
| EP | 1344488 | 9/2003 |

(Continued)

OTHER PUBLICATIONS

Stagg and Gennser, "Electronic Analysis of Foetal Breathing Movements: A practical Application of Phase-Locked-Loop Principles," Journal of Med. Eng. and Tech., Sep. 1978, vol. 2, No. 5, pp. 246-249.

(Continued)

*Primary Examiner* — Christopher A Flory
(74) *Attorney, Agent, or Firm* — Cantor Colburn LLP

(57) ABSTRACT

Systems and methods are provided for determining respiration information from physiological signals such as PPG signals. A physiological signal is processed to generate at least one respiration information signal and an autocorrelation sequence is generated based on the at least one respiration information signal. In some embodiments, a respiration peak is identified based on the autocorrelation sequence and a composite peak is generated based on the identified peak and at least one previous respiration peak. Respiration information is calculated based on the composite peak. In some embodiments, a determination is made whether the autocorrelation sequence includes an undesired harmonic. When the autocorrelation sequence includes an undesired harmonic, the autocorrelation sequence may not be used in the calculation of respiration information.

20 Claims, 11 Drawing Sheets

Related U.S. Application Data

(60) Provisional application No. 61/942,564, filed on Feb. 20, 2014.

(51) Int. Cl.
*A61B 5/1455* (2006.01)
*A61B 5/024* (2006.01)

(52) U.S. Cl.
CPC ........ *A61B 5/14551* (2013.01); *A61B 5/7203* (2013.01); *A61B 5/7278* (2013.01)

(58) Field of Classification Search
USPC .................................................. 600/476, 529
See application file for complete search history.

(56) References Cited

U.S. PATENT DOCUMENTS

| | | | |
|---|---|---|---|
| 5,285,784 A | 2/1994 | Secker | |
| 5,368,026 A | 11/1994 | Swedlow et al. | |
| 5,398,682 A | 3/1995 | Lynn | |
| 5,558,096 A | 9/1996 | Palatnik | |
| 5,584,295 A | 12/1996 | Muller et al. | |
| 5,588,425 A | 12/1996 | Sackner et al. | |
| 5,605,151 A | 2/1997 | Lynn | |
| 5,862,805 A | 1/1999 | Nitzan | |
| 5,865,736 A | 2/1999 | Baker, Jr. et al. | |
| 5,891,023 A | 4/1999 | Lynn | |
| 6,002,952 A | 12/1999 | Diab et al. | |
| 6,035,223 A | 3/2000 | Baker, Jr. | |
| 6,081,742 A | 6/2000 | Amano et al. | |
| 6,095,984 A | 8/2000 | Amano et al. | |
| 6,129,675 A | 10/2000 | Jay | |
| 6,135,966 A | 10/2000 | Ko | |
| 6,178,261 B1 | 1/2001 | Williams et al. | |
| 6,223,064 B1 | 4/2001 | Lynn | |
| 6,229,856 B1 | 5/2001 | Diab et al. | |
| 6,238,351 B1 | 5/2001 | Orr et al. | |
| 6,325,761 B1 | 12/2001 | Jay | |
| 6,334,065 B1 | 12/2001 | Al-Ali et al. | |
| 6,342,039 B1 | 1/2002 | Lynn | |
| 6,350,242 B1 | 2/2002 | Doten et al. | |
| 6,405,076 B1 | 6/2002 | Taylor et al. | |
| 6,463,311 B1 | 10/2002 | Diab | |
| 6,506,153 B1 | 1/2003 | Littek et al. | |
| 6,561,986 B2 | 5/2003 | Baura et al. | |
| 6,564,077 B2 | 5/2003 | Mortara | |
| 6,606,511 B1 | 8/2003 | Ali et al. | |
| 6,609,016 B1 | 8/2003 | Lynn | |
| 6,684,090 B2 | 1/2004 | Ali et al. | |
| 6,694,178 B1 | 2/2004 | Soula et al. | |
| 6,702,752 B2 | 3/2004 | Dekker | |
| 6,709,402 B2 | 3/2004 | Dekker | |
| 6,748,252 B2 | 6/2004 | Lynn | |
| 6,754,516 B2 | 6/2004 | Mannheimer | |
| 6,760,608 B2 | 7/2004 | Lynn | |
| 6,783,498 B2 | 8/2004 | Sackner et al. | |
| 6,816,741 B2 | 11/2004 | Diab | |
| 6,839,581 B1 | 1/2005 | Ei-Solh et al. | |
| 6,850,787 B2 | 2/2005 | Weber | |
| 6,896,661 B2 | 5/2005 | Dekker | |
| 6,905,470 B2 | 6/2005 | Lee et al. | |
| 6,925,324 B2 | 8/2005 | Shusterman | |
| 6,931,269 B2 | 8/2005 | Terry | |
| 6,966,878 B2 | 11/2005 | Schoisswohl et al. | |
| 6,970,792 B1 | 11/2005 | Diab | |
| 6,980,679 B2 | 12/2005 | Jeung et al. | |
| 7,020,507 B2 | 3/2006 | Scharf et al. | |
| 7,035,679 B2 | 4/2006 | Addison et al. | |
| 7,043,293 B1 | 5/2006 | Baura | |
| 7,044,918 B2 | 5/2006 | Diab | |
| 7,070,566 B2 | 7/2006 | Medero et al. | |
| 7,079,888 B2 | 7/2006 | Dung et al. | |
| 7,147,601 B2 | 12/2006 | Marks et al. | |
| 7,177,682 B2 | 2/2007 | Lovett | |
| 7,190,261 B2 | 3/2007 | Al-Ali | |
| 7,215,986 B2 | 5/2007 | Diab et al. | |
| 7,218,966 B2 | 5/2007 | Haefner | |
| 7,254,425 B2 | 8/2007 | Lowery et al. | |
| 7,283,870 B2 | 10/2007 | Kaiser et al. | |
| 7,315,753 B2 | 1/2008 | Baker, Jr. et al. | |
| 7,336,982 B2 | 2/2008 | Yoo | |
| 7,355,512 B1 | 4/2008 | Al-Ali | |
| 7,367,339 B2 | 5/2008 | Hickle | |
| 7,367,949 B2 | 5/2008 | Korhonen et al. | |
| 7,398,115 B2 | 7/2008 | Lynn | |
| 7,403,806 B2 | 7/2008 | Norris | |
| 7,407,486 B2 | 8/2008 | Huiku et al. | |
| 7,415,297 B2 | 8/2008 | Al-Ali et al. | |
| 7,438,683 B2 | 10/2008 | Al-Ali et al. | |
| 7,440,787 B2 | 10/2008 | Diab | |
| 7,470,235 B2 | 12/2008 | Moriya et al. | |
| 7,485,095 B2 | 2/2009 | Shusterman | |
| 7,496,393 B2 | 2/2009 | Diab et al. | |
| 7,499,835 B2 | 3/2009 | Weber et al. | |
| 7,523,011 B2 | 4/2009 | Akiyama et al. | |
| 7,561,912 B2 | 7/2009 | Schatz et al. | |
| 7,610,324 B2 | 10/2009 | Troyansky et al. | |
| 7,690,378 B1 | 4/2010 | Turcott | |
| 7,801,591 B1 | 9/2010 | Shusterman | |
| 7,869,980 B2 | 1/2011 | Casler et al. | |
| 7,894,868 B2 | 2/2011 | Al-Ali et al. | |
| 7,899,507 B2 | 3/2011 | Al-Ali et al. | |
| 7,904,132 B2 | 3/2011 | Weber | |
| 7,931,599 B2 | 4/2011 | Baker, Jr. et al. | |
| 7,976,472 B2 | 7/2011 | Kiani | |
| 7,988,637 B2 | 8/2011 | Diab | |
| 8,019,400 B2 | 9/2011 | Diab et al. | |
| 8,046,040 B2 | 10/2011 | Ali et al. | |
| 8,130,105 B2 | 3/2012 | Al-Ali et al. | |
| 8,203,438 B2 | 6/2012 | Kiani et al. | |
| 8,226,568 B2 | 7/2012 | Watson et al. | |
| 8,275,553 B2 | 9/2012 | Ochs et al. | |
| 8,364,225 B2 | 1/2013 | Addison et al. | |
| 8,636,667 B2 | 1/2014 | Ochs et al. | |
| 9,119,597 B2 | 9/2015 | Dripps et al. | |
| 2002/0117173 A1 | 8/2002 | Lynn | |
| 2003/0036685 A1 | 2/2003 | Goodman | |
| 2003/0158466 A1 | 8/2003 | Lynn | |
| 2003/0163054 A1 | 8/2003 | Dekker | |
| 2004/0015091 A1 | 1/2004 | Greenwald et al. | |
| 2005/0004479 A1 | 1/2005 | Townsend et al. | |
| 2005/0022606 A1 | 2/2005 | Partin et al. | |
| 2005/0027205 A1 | 2/2005 | Tarassenko et al. | |
| 2005/0049470 A1 | 3/2005 | Terry | |
| 2005/0070774 A1 | 3/2005 | Addison | |
| 2005/0222502 A1 | 10/2005 | Cooper | |
| 2005/0222503 A1 | 10/2005 | Dunlop et al. | |
| 2006/0122476 A1 | 6/2006 | Van Slyke | |
| 2006/0192667 A1 | 8/2006 | Al-Ali | |
| 2006/0211930 A1 | 9/2006 | Scharf et al. | |
| 2006/0217614 A1 | 9/2006 | Takala et al. | |
| 2006/0258921 A1 | 11/2006 | Addison et al. | |
| 2007/0004977 A1 | 1/2007 | Norris | |
| 2007/0010723 A1 | 1/2007 | Uutela et al. | |
| 2007/0032733 A1 | 2/2007 | Burton | |
| 2007/0073120 A1 | 3/2007 | Li et al. | |
| 2007/0073124 A1 | 3/2007 | Li et al. | |
| 2007/0129636 A1 | 6/2007 | Friedman et al. | |
| 2007/0149890 A1 | 6/2007 | Li et al. | |
| 2007/0179369 A1 | 8/2007 | Baker, Jr. | |
| 2007/0213619 A1 | 9/2007 | Linder | |
| 2007/0213621 A1 | 9/2007 | Reisfeld et al. | |
| 2007/0255146 A1 | 11/2007 | Andrews et al. | |
| 2007/0282212 A1* | 12/2007 | Sierra ............... | A61B 5/0205 600/529 |
| 2007/0293896 A1 | 12/2007 | Haefner | |
| 2008/0013747 A1 | 1/2008 | Tran | |
| 2008/0077022 A1 | 3/2008 | Baker | |
| 2008/0167540 A1 | 7/2008 | Korhonen et al. | |
| 2008/0171946 A1* | 7/2008 | Hansmann ......... | A61B 5/024 600/529 |
| 2008/0200775 A1 | 8/2008 | Lynn | |
| 2009/0247837 A1 | 10/2009 | Ochs et al. | |

(56) References Cited

U.S. PATENT DOCUMENTS

| | | |
|---|---|---|
| 2009/0326349 A1 | 12/2009 | McGonigle et al. |
| 2009/0326395 A1 | 12/2009 | Watson |
| 2009/0326831 A1 | 12/2009 | McGonigle et al. |
| 2010/0014761 A1 | 1/2010 | Addison et al. |
| 2010/0113904 A1 | 5/2010 | Batchelder et al. |
| 2010/0113908 A1 | 5/2010 | Vargas et al. |
| 2010/0113909 A1 | 5/2010 | Batchelder et al. |
| 2010/0286495 A1 | 11/2010 | McGonigle et al. |
| 2011/0066062 A1 | 3/2011 | Banet et al. |
| 2011/0071406 A1 | 3/2011 | Addison |
| 2012/0123689 A1 | 5/2012 | Addison et al. |
| 2013/0041240 A1 | 2/2013 | Addison et al. |
| 2013/0079606 A1 | 3/2013 | McGonigle et al. |
| 2013/0079647 A1 | 3/2013 | McGonigle et al. |
| 2013/0079656 A1 | 3/2013 | Dripps et al. |
| 2013/0079657 A1 | 3/2013 | Ochs et al. |
| 2013/0080489 A1 | 3/2013 | Ochs et al. |
| 2013/0137936 A1 | 5/2013 | Baker, Jr. et al. |
| 2013/0172767 A1 | 7/2013 | Dripps et al. |
| 2013/0231574 A1 | 9/2013 | Tran |
| 2013/0289413 A1 | 10/2013 | Ochs et al. |
| 2013/0324812 A1* | 12/2013 | Brainard, II ......... A61B 5/0205 600/324 |
| 2014/0073863 A1 | 3/2014 | Engelbrecht et al. |
| 2014/0073864 A1 | 3/2014 | Engelbrecht et al. |
| 2014/0073866 A1 | 3/2014 | Engelbrecht et al. |
| 2014/0073870 A1 | 3/2014 | Engelbrecht et al. |
| 2014/0073875 A1 | 3/2014 | Engelbrecht et al. |
| 2014/0073876 A1 | 3/2014 | Rodriguez-Llorente et al. |
| 2014/0073877 A1 | 3/2014 | Wooder |
| 2014/0073878 A1 | 3/2014 | Engelbrecht et al. |
| 2014/0073898 A1 | 3/2014 | Engelbrecht et al. |
| 2014/0073939 A1 | 3/2014 | Rodriguez-Llorente et al. |
| 2014/0073948 A1 | 3/2014 | Engelbrecht et al. |
| 2014/0073949 A1 | 3/2014 | Engelbrecht et al. |
| 2014/0073951 A1 | 3/2014 | Engelbrecht et al. |
| 2014/0073953 A1 | 3/2014 | Engelbrecht et al. |
| 2014/0073954 A1 | 3/2014 | Engelbrecht et al. |
| 2014/0073955 A1 | 3/2014 | Engelbrecht et al. |
| 2014/0073956 A1 | 3/2014 | Engelbrecht et al. |
| 2014/0073960 A1 | 3/2014 | Rodriguez-Llorente et al. |
| 2014/0073961 A1 | 3/2014 | Rodriguez-Llorente et al. |
| 2014/0073963 A1 | 3/2014 | Engelbrecht et al. |
| 2014/0073965 A1 | 3/2014 | Engelbrecht et al. |
| 2014/0073966 A1 | 3/2014 | Engelbrecht et al. |
| 2014/0073967 A1 | 3/2014 | Engelbrecht et al. |
| 2014/0073968 A1 | 3/2014 | Engelbrecht et al. |
| 2014/0073974 A1 | 3/2014 | Engelbrecht |
| 2014/0073975 A1 | 3/2014 | Engelbrecht et al. |
| 2014/0175261 A1 | 6/2014 | Addison et al. |
| 2014/0221851 A1 | 8/2014 | Van Slyke et al. |
| 2014/0221852 A1 | 8/2014 | Van Slyke et al. |
| 2014/0244205 A1 | 8/2014 | Van Slyke et al. |
| 2014/0249429 A1 | 9/2014 | Tran |
| 2014/0266695 A1 | 9/2014 | Addison |
| 2015/0112605 A1 | 4/2015 | Watson et al. |
| 2015/0119664 A1 | 4/2015 | Addison et al. |
| 2016/0317089 A1 | 11/2016 | Fyfe et al. |

FOREIGN PATENT DOCUMENTS

| | | |
|---|---|---|
| EP | 1507474 | 2/2009 |
| WO | 00/21438 | 4/2000 |
| WO | 03/000125 | 1/2003 |
| WO | 03/055395 | 7/2003 |
| WO | 03/084396 | 10/2003 |
| WO | 04/075746 | 9/2004 |
| WO | 2010030238 A1 | 3/2010 |

OTHER PUBLICATIONS

Rapaport and Cousin, "New Phase-Lock Tracking Instrument for Foetal Breathing Monitoring," Med. & Biol. Eng. & Camp. 1982, vol. 20, pp. 1-6.

Lindberg, L.G., Ughall, H., Oberg, P.A., "Monitoring of Respiratory and Heart Rates Using a Fibre-Optic Sensor," Medical & Biological Engineering & Computing, Sep. 1992, pp. 533-537.

International Search Report and Written Opinion of the International Searching Authority for application No. PCT/US2015/016924 dated Jul. 27, 2015.

* cited by examiner

SYSTEMS AND METHODS FOR FILTERING AUTOCORRELATION PEAKS AND DETECTING HARMONICS

CROSS REFERENCE TO RELATED APPLICATION

This application is a continuation of U.S. application Ser. No. 14/628,004, filed on Feb. 20, 2015, which claims priority to U.S. Provisional Application No. 61/942,564, filed on Feb. 20, 2014, the entire contents of which are herein expressly incorporated by reference for all purposes.

The present disclosure relates to processing physiological signals, and more particularly relates to determining respiration information from a physiological signal.

SUMMARY

Systems and methods are provided for determining respiration information based on a received signal. The received signal may be processed to generate an autocorrelation sequence. In some embodiments, the autocorrelation sequence may be analyzed to determine whether it includes undesired harmonics and the processing may be modified when undesired harmonics are present. In some embodiments, a respiration peak is identified from the autocorrelation sequence and a composite peak is generated based on the identified peak and at least one previous respiration peak. Respiration information may be calculated based on the composite peak.

In some embodiments, a method is provided determining respiration information. The method may be performed with processing equipment. The method comprises receiving a photoplethysmograph (PPG) signal and processing the PPG signal to generate at least one respiration information signal. The method further comprises generating an autocorrelation sequence based on the at least one respiration information signal and identifying a respiration peak of the autocorrelation sequence. The method further comprises generating a composite peak based on the respiration peak and at least one previous respiration peak and calculating the respiration information based at least in part on the composite peak.

In some embodiments, a system is provided for determining respiration information. The system comprises an input for receiving a PPG signal and processing equipment. The processing equipment is configured for processing the PPG signal to generate at least one respiration information signal and generating an autocorrelation sequence based on the at least one respiration information signal. The processing equipment is further configured for identifying a respiration peak of the autocorrelation sequence and generating a composite peak based on the respiration peak and at least one previous respiration peak. The processing equipment is further configured for calculating the respiration information based at least in part on the composite peak.

In some embodiments, a method is provided for determining respiration information. The method may be performed with processing equipment. The method comprises receiving a PPG signal and processing the PPG signal to generate at least one respiration information signal. The method further comprises generating an autocorrelation sequence based on the at least one respiration information signal and determining whether the autocorrelation sequence includes an undesired harmonic. The method further comprises calculating the respiration information based at least in part on the autocorrelation sequence when it is determined that the autocorrelation sequence does not include an undesired harmonic.

In some embodiments, a system is provided for determining respiration information. The system comprises an input for receiving a PPG signal and processing equipment. The processing equipment is configured for processing the PPG signal to generate at least one respiration information signal and generating an autocorrelation sequence based on the at least one respiration information signal. The processing equipment is further configured for determining whether the autocorrelation sequence includes an undesired harmonic and calculating the respiration information based at least in part on the autocorrelation sequence when it is determined that the autocorrelation sequence does not include an undesired harmonic.

BRIEF DESCRIPTION OF THE FIGURES

The above and other features of the present disclosure, its nature and various advantages will be more apparent upon consideration of the following detailed description, taken in conjunction with the accompanying drawings in which.

DETAILED DESCRIPTION OF THE FIGURES

Figure 1:
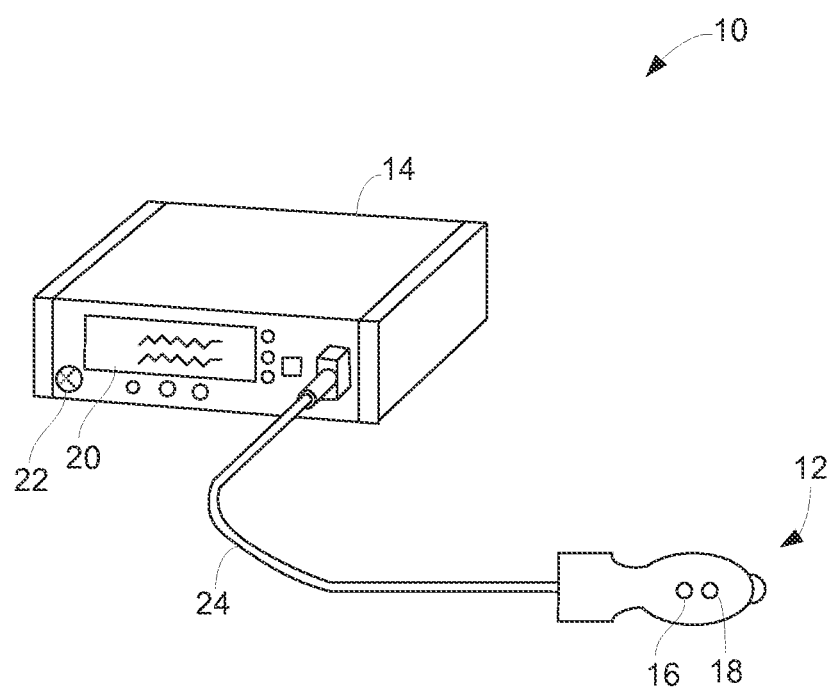
FIG. 1 shows a perspective view of an illustrative patient monitoring system in accordance with some embodiments of the present disclosure.

A physiological signal such as a photoplethysmograph (PPG) signal may be indicative of pulsatile blood flow.

Pulsatile blood flow may be dependent on a number of physiological functions such as cardiovascular function and respiration. For example, the PPG signal may exhibit a periodic component that generally corresponds to the heart beat of a patient. This pulsatile component of the PPG signal may be used to determine physiological parameters such as heart rate.

Respiration may also impact the pulsatile blood flow that is indicated by the PPG signal. It may thus be possible to calculate respiration information such as respiration rate from the PPG signal. However, in some instances a respiration rate value calculated from the most recently received data may be inaccurate or incorrect, for example, based on noise in the received signal, short-term variations in the patient's breathing pattern, measurement error, or other related factors. It may therefore be desirable to utilize both the most recently received data as well as previous data to determine respiration information such as respiration rate. Accordingly, it may be desirable to determine the confidence in the most recently received data and generate a composite value including previous data based at least in part on the confidence.

For purposes of clarity, the present disclosure is written in the context of the physiological signal being a PPG signal generated by a pulse oximetry system. It will be understood that any other suitable physiological signal or any other suitable system may be used in accordance with the teachings of the present disclosure.

An oximeter is a medical device that may determine the oxygen saturation of the blood. One common type of oximeter is a pulse oximeter, which may indirectly measure the oxygen saturation of a patient's blood (as opposed to measuring oxygen saturation directly by analyzing a blood sample taken from the patient). Pulse oximeters may be included in patient monitoring systems that measure and display various blood flow characteristics including, but not limited to, the oxygen saturation of hemoglobin in arterial blood. Such patient monitoring systems may also measure and display additional physiological parameters, such as a patient's pulse rate.

An oximeter may include a light sensor that is placed at a site on a patient, typically a fingertip, toe, forehead or earlobe, or in the case of a neonate, across a foot. The oximeter may use a light source to pass light through blood perfused tissue and photoelectrically sense the absorption of the light in the tissue. In addition, locations that are not typically understood to be optimal for pulse oximetry serve as suitable sensor locations for the monitoring processes described herein, including any location on the body that has a strong pulsatile arterial flow. For example, additional suitable sensor locations include, without limitation, the neck to monitor carotid artery pulsatile flow, the wrist to monitor radial artery pulsatile flow, the inside of a patient's thigh to monitor femoral artery pulsatile flow, the ankle to monitor tibial artery pulsatile flow, and around or in front of the ear. Suitable sensors for these locations may include sensors for sensing absorbed light based on detecting reflected light. In all suitable locations, for example, the oximeter may measure the intensity of light that is received at the light sensor as a function of time. The oximeter may also include sensors at multiple locations. A signal representing light intensity versus time or a mathematical manipulation of this signal (e.g., a scaled version thereof, a log taken thereof, a scaled version of a log taken thereof, etc.) may be referred to as the photoplethysmograph (PPG) signal. In addition, the term "PPG signal," as used herein, may also refer to an absorption signal (i.e., representing the amount of light absorbed by the tissue) or any suitable mathematical manipulation thereof. The light intensity or the amount of light absorbed may then be used to calculate any of a number of physiological parameters, including an amount of a blood constituent (e.g., oxyhemoglobin) being measured as well as a pulse rate and when each individual pulse occurs.

In some applications, the light passed through the tissue is selected to be of one or more wavelengths that are absorbed by the blood in an amount representative of the amount of the blood constituent present in the blood. The amount of light passed through the tissue varies in accordance with the changing amount of blood constituent in the tissue and the related light absorption. Red and infrared (IR) wavelengths may be used because it has been observed that highly oxygenated blood will absorb relatively less Red light and more IR light than blood with a lower oxygen saturation. By comparing the intensities of two wavelengths at different points in the pulse cycle, it is possible to estimate the blood oxygen saturation of hemoglobin in arterial blood.

When the measured blood parameter is the oxygen saturation of hemoglobin, a convenient starting point assumes a saturation calculation based at least in part on Lambert-Beer's law. The following notation will be used herein:

$$I(\lambda,t)=I_0(\lambda)\exp(-(s\beta_0(\lambda)+(1-s)\beta_r(\lambda))l(t)) \tag{1}$$

where:
$\lambda$=wavelength;
t=time;
I=intensity of light detected;
$I_0$=intensity of light transmitted;
s=oxygen saturation;
$\beta_0$, $\beta_r$=empirically derived absorption coefficients; and
l(t)=a combination of concentration and path length from emitter to detector as a function of time.

The traditional approach measures light absorption at two wavelengths (e.g., Red and IR), and then calculates saturation by solving for the "ratio of ratios" as follows.

1. The natural logarithm of Eq. 1 is taken ("log" will be used to represent the natural logarithm) for IR and Red to yield $$\log I = \log I_o - (s\beta_o + (1-s)\beta_r)l. \tag{2}$$

2. Eq. 2 is then differentiated with respect to time to yield $$\frac{d \log I}{dt} = -(s\beta_O + (1-s)\beta_r)\frac{dl}{dt}. \tag{3}$$

3. Eq. 3, evaluated at the Red wavelength $\lambda_R$, is divided by Eq. 3 evaluated at the IR wavelength 2, in accordance with $$\frac{d \log I(\lambda_R)/dt}{d \log I(\lambda_{IR})/dt} = \frac{s\beta_O(\lambda_R) + (1-s)\beta_r(\lambda_R)}{s\beta_O(\lambda_{IR}) + (1-s)\beta_r(\lambda_{IR})}. \tag{4}$$

4. Solving for s yields $$s = \frac{\frac{d \log I(\lambda_{IR})}{dt}\beta_r(\lambda_R) - \frac{d \log I(\lambda_R)}{dt}\beta_r(\lambda_{IR})}{\frac{d \log I(\lambda_R)}{dt}(\beta_O(\lambda_{IR}) - \beta_r(\lambda_{IR})) - \frac{d \log I(\lambda_{IR})}{dt}(\beta_O(\lambda_R) - \beta_r(\lambda_R))}. \tag{5}$$

5. Note that, in discrete time, the following approximation can be made:

$$\frac{d \log I(\lambda, t)}{dt} \simeq \log I(\lambda, t_2) - \log I(\lambda, t_1). \quad (6)$$

6. Rewriting Eq. 6 by observing that log A−log B=log(A/B) yields $$\frac{d \log I(\lambda, t)}{dt} \simeq \log\left(\frac{I(t_2, \lambda)}{I(t_1, \lambda)}\right). \quad (7)$$

7. Thus, Eq. 4 can be expressed as $$\frac{\frac{d \log I(\lambda_R)}{dt}}{\frac{d \log I(\lambda_{IR})}{dt}} \simeq \frac{\log\left(\frac{I(t_1, \lambda_R)}{I(t_2, \lambda_R)}\right)}{\log\left(\frac{I(t_1, \lambda_{IR})}{I(t_2, \lambda_{IR})}\right)} = R, \quad (8)$$

where R represents the "ratio of ratios."

8. Solving Eq. 4 for s using the relationship of Eq. 5 yields $$s = \frac{\beta_r(\lambda_R) - R\beta_r(\lambda_{IR})}{R(\beta_O(\lambda_{IR}) - \beta_r(\lambda_{IR})) - \beta_O(\lambda_R) + \beta_r(\lambda_R)}. \quad (9)$$

9. From Eq. 8, R can be calculated using two points (e.g., PPG maximum and minimum), or a family of points. One method applies a family of points to a modified version of Eq. 8. Using the relationship $$\frac{d \log I}{dt} = \frac{dI/dt}{I}, \quad (10)$$

Eq. 8 becomes $$\frac{\frac{d \log I(\lambda_R)}{dt}}{\frac{d \log I(\lambda_{IR})}{dt}} \simeq \frac{\frac{I(t_2, \lambda_R) - I(t_1, \lambda_R)}{I(t_1, \lambda_R)}}{\frac{I(t_2, \lambda_{IR}) - I(t_1, \lambda_{IR})}{I(t_1, \lambda_{IR})}}$$

$$= \frac{[I(t_2, \lambda_R) - I(t_1, \lambda_R)]I(t_1, \lambda_{IR})}{[I(t_2, \lambda_{IR}) - I(t_1, \lambda_{IR})]I(t_1, \lambda_R)}$$

$$= R, \quad (11)$$

which defines a cluster of points whose slope of y versus x will give R when $$x = [I(t_2, \lambda_{IR}) - I(t_1, \lambda_{IR})]I(t_1, \lambda_R), \quad (12)$$

and $$y = [I(t_2, \lambda_R) - I(t_1, \lambda_R)]I(t_1, \lambda_{IR}). \quad (13)$$

Once R is determined or estimated, for example, using the techniques described above, the blood oxygen saturation can be determined or estimated using any suitable technique for relating a blood oxygen saturation value to R. For example, blood oxygen saturation can be determined from empirical data that may be indexed by values of R, and/or it may be determined from curve fitting and/or other interpolative techniques.

FIG. 1 is a perspective view of an embodiment of a patient monitoring system 10. System 10 may include sensor unit 12 and monitor 14. In some embodiments, sensor unit 12 may be part of an oximeter. Sensor unit 12 may include an emitter 16 for emitting light at one or more wavelengths into a patient's tissue. A detector 18 may also be provided in sensor unit 12 for detecting the light originally from emitter 16 that emanates from the patient's tissue after passing through the tissue. Any suitable physical configuration of emitter 16 and detector 18 may be used. In an embodiment, sensor unit 12 may include multiple emitters and/or detectors, which may be spaced apart. System 10 may also include one or more additional sensor units (not shown) that may take the form of any of the embodiments described herein with reference to sensor unit 12. An additional sensor unit may be the same type of sensor unit as sensor unit 12, or a different sensor unit type than sensor unit 12. Multiple sensor units may be capable of being positioned at two different locations on a subject's body; for example, a first sensor unit may be positioned on a patient's forehead, while a second sensor unit may be positioned at a patient's fingertip.

Sensor units may each detect any signal that carries information about a patient's physiological state, such as an electrocardiograph signal, arterial line measurements, or the pulsatile force exerted on the walls of an artery using, for example, oscillometric methods with a piezoelectric transducer. According to some embodiments, system 10 may include two or more sensors forming a sensor array in lieu of either or both of the sensor units. Each of the sensors of a sensor array may be a complementary metal oxide semiconductor (CMOS) sensor. Alternatively, each sensor of an array may be charged coupled device (CCD) sensor. In some embodiments, a sensor array may be made up of a combination of CMOS and CCD sensors. The CCD sensor may comprise a photoactive region and a transmission region for receiving and transmitting data whereas the CMOS sensor may be made up of an integrated circuit having an array of pixel sensors. Each pixel may have a photodetector and an active amplifier. It will be understood that any type of sensor, including any type of physiological sensor, may be used in one or more sensor units in accordance with the systems and techniques disclosed herein. It is understood that any number of sensors measuring any number of physiological signals may be used to determine physiological information in accordance with the techniques described herein.

In some embodiments, emitter 16 and detector 18 may be on opposite sides of a digit such as a finger or toe, in which case the light that is emanating from the tissue has passed completely through the digit. In some embodiments, emitter 16 and detector 18 may be arranged so that light from emitter 16 penetrates the tissue and is reflected by the tissue into detector 18, such as in a sensor designed to obtain pulse oximetry data from a patient's forehead.

In some embodiments, sensor unit 12 may be connected to and draw its power from monitor 14 as shown. In another embodiment, the sensor may be wirelessly connected to monitor 14 and include its own battery or similar power supply (not shown). Monitor 14 may be configured to calculate physiological parameters (e.g., pulse rate, blood oxygen saturation (e.g., $SpO_2$), and respiration information) based at least in part on data relating to light emission and detection received from one or more sensor units such as sensor unit 12 and an additional sensor (not shown). In some embodiments, the calculations may be performed on the sensor units or an intermediate device and the result of the calculations may be passed to monitor 14. Further, monitor 14 may include a display 20 configured to display the physiological parameters or other information about the system. In the embodiment shown, monitor 14 may also include a speaker 22 to provide an audible sound that may be used in various other embodiments, such as for example, sounding an audible alarm in the event that a patient's physiological parameters are not within a predefined normal range. In some embodiments, the system 10 includes a stand-alone monitor in communication with the monitor 14 via a cable or a wireless network link.

In some embodiments, sensor unit 12 may be communicatively coupled to monitor 14 via a cable 24. In some embodiments, a wireless transmission device (not shown) or the like may be used instead of or in addition to cable 24. Monitor 14 may include a sensor interface configured to receive physiological signals from sensor unit 12, provide signals and power to sensor unit 12, or otherwise communicate with sensor unit 12. The sensor interface may include any suitable hardware, software, or both, which may allow communication between monitor 14 and sensor unit 12.

As is described herein, monitor 14 may generate a PPG signal based on the signal received from sensor unit 12. The PPG signal may consist of data points that represent a pulsatile waveform. The pulsatile waveform may be modulated based on the respiration of a patient. Respiratory modulations may include baseline modulations, amplitude modulations, frequency modulations, respiratory sinus arrhythmia, any other suitable modulations, or any combination thereof. Respiratory modulations may exhibit different phases, amplitudes, or both, within a PPG signal and may contribute to complex behavior (e.g., changes) of the PPG signal. For example, the amplitude of the pulsatile waveform may be modulated based on respiration (amplitude modulation), the frequency of the pulsatile waveform may be modulated based on respiration (frequency modulation), and a signal baseline for the pulsatile waveform may be modulated based on respiration (baseline modulation). Monitor 14 may analyze the PPG signal (e.g., by generating respiration morphology signals from the PPG signal, generating a combined autocorrelation sequence based on the respiration morphology signals, and calculating respiration information from the combined autocorrelation sequence) to determine respiration information based on one or more of these modulations of the PPG signal.

As is described herein, respiration information may be determined from the PPG signal by monitor 14. However, it will be understood that the PPG signal could be transmitted to any suitable device for the determination of respiration information, such as a local computer, a remote computer, a nurse station, mobile devices, tablet computers, or any other device capable of sending and receiving data and performing processing operations. Information may be transmitted from monitor 14 in any suitable manner, including wireless (e.g., WiFi, Bluetooth, etc.), wired (e.g., USB, Ethernet, etc.), or application-specific connections. The receiving device may determine respiration information as described herein.

Figure 2:
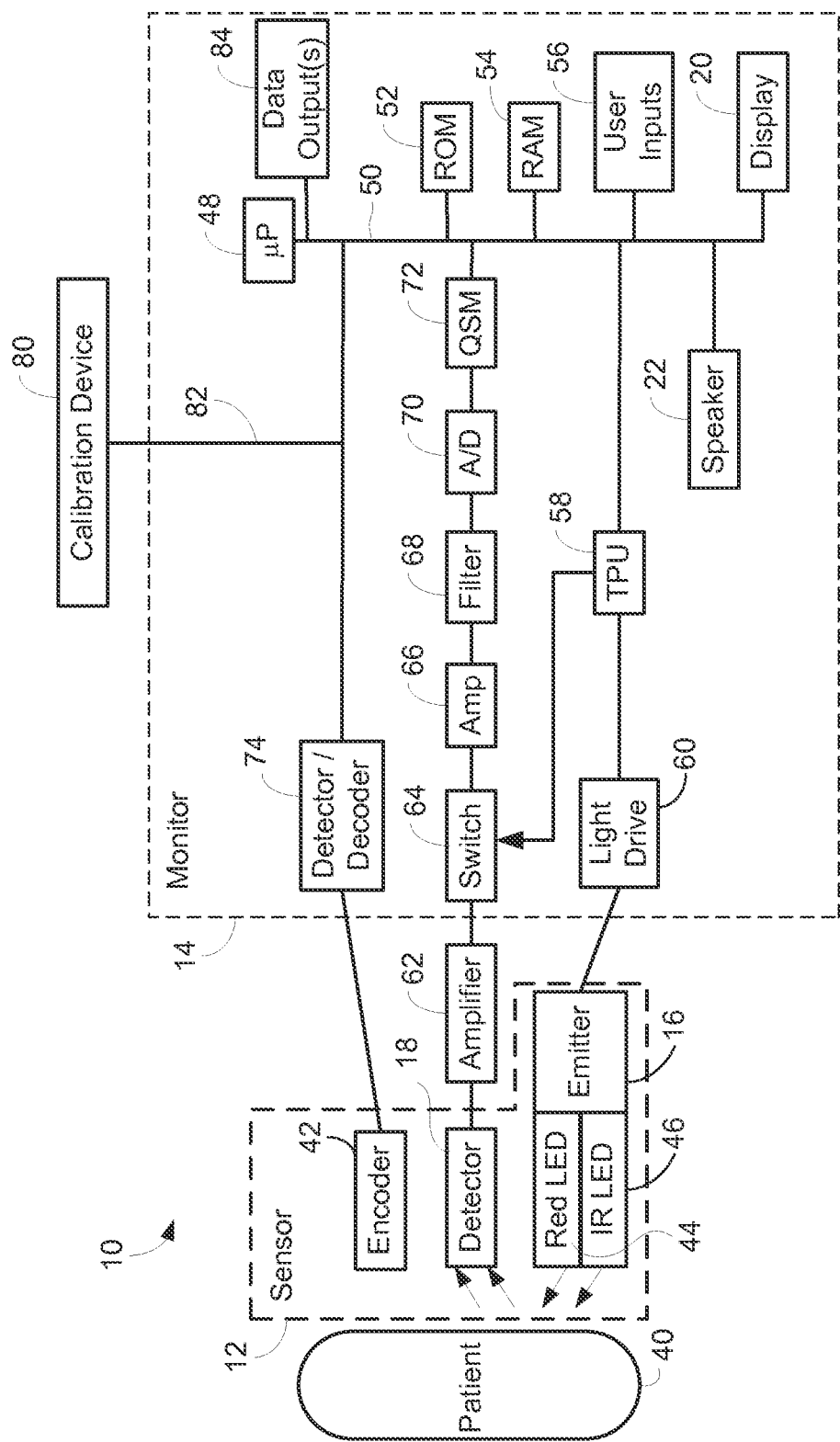
FIG. 2 shows a block diagram of the illustrative patient monitoring system of FIG. 1 coupled to a patient in accordance with some embodiments of the present disclosure.

FIG. 2 shows a block diagram of a patient monitoring system, such as patient monitoring system 10 of FIG. 1, which may be coupled to a patient 40 in accordance with an embodiment. Certain illustrative components of sensor unit 12 and monitor 14 are illustrated in FIG. 2.

Sensor unit 12 may include emitter 16, detector 18, and encoder 42. In the embodiment shown, emitter 16 may be configured to emit at least two wavelengths of light (e.g., Red and IR) into a patient's tissue 40. Hence, emitter 16 may include a Red light emitting light source such as Red light emitting diode (LED) 44 and an IR light emitting light source such as IR LED 46 for emitting light into the patient's tissue 40 at the wavelengths used to calculate the patient's physiological parameters. In some embodiments, the Red wavelength may be between about 600 nm and about 700 nm, and the IR wavelength may be between about 800 nm and about 1000 nm. In embodiments where a sensor array is used in place of a single sensor, each sensor may be configured to emit a single wavelength. For example, a first sensor may emit only a Red light while a second sensor may emit only an IR light. In a further example, the wavelengths of light used may be selected based on the specific location of the sensor.

It will be understood that, as used herein, the term "light" may refer to energy produced by radiation sources and may include one or more of radio, microwave, millimeter wave, infrared, visible, ultraviolet, gamma ray or X-ray electromagnetic radiation. As used herein, light may also include electromagnetic radiation having any wavelength within the radio, microwave, infrared, visible, ultraviolet, or X-ray spectra, and that any suitable wavelength of electromagnetic radiation may be appropriate for use with the present techniques. Detector 18 may be chosen to be specifically sensitive to the chosen targeted energy spectrum of the emitter 16.

In some embodiments, detector 18 may be configured to detect the intensity of light at the Red and IR wavelengths. Alternatively, each sensor in the array may be configured to detect an intensity of a single wavelength. In operation, light may enter detector 18 after passing through the patient's tissue 40. Detector 18 may convert the intensity of the received light into an electrical signal. The light intensity is directly related to the absorbance and/or reflectance of light in the tissue 40. That is, when more light at a certain wavelength is absorbed or reflected, less light of that wavelength is received from the tissue by the detector 18. After converting the received light to an electrical signal, detector 18 may send the signal to monitor 14, where physiological parameters may be calculated based on the absorption of the Red and IR wavelengths in the patient's tissue 40.

In some embodiments, encoder 42 may contain information about sensor unit 12, such as what type of sensor it is (e.g., whether the sensor is intended for placement on a forehead or digit) and the wavelengths of light emitted by emitter 16. This information may be used by monitor 14 to select appropriate algorithms, lookup tables and/or calibration coefficients stored in monitor 14 for calculating the patient's physiological parameters.

Encoder 42 may contain information specific to patient 40, such as, for example, the patient's age, weight, and diagnosis. This information about a patient's characteristics may allow monitor 14 to determine, for example, patient-specific threshold ranges in which the patient's physiological parameter measurements should fall and to enable or disable additional physiological parameter algorithms. This information may also be used to select and provide coefficients for equations from which measurements may be determined based at least in part on the signal or signals received at sensor unit 12. For example, some pulse oximetry sensors rely on equations to relate an area under a portion of a PPG signal corresponding to a physiological pulse to determine blood pressure. These equations may contain coefficients that depend upon a patient's physiological characteristics as stored in encoder 42.

Encoder 42 may, for instance, be a coded resistor that stores values corresponding to the type of sensor unit 12 or the type of each sensor in the sensor array, the wavelengths of light emitted by emitter 16 on each sensor of the sensor array, and/or the patient's characteristics and treatment information. In some embodiments, encoder 42 may include a memory on which one or more of the following information may be stored for communication to monitor 14; the type of the sensor unit 12; the wavelengths of light emitted by emitter 16; the particular wavelength each sensor in the sensor array is monitoring; a signal threshold for each sensor in the sensor array; any other suitable information; physiological characteristics (e.g., gender, age, weight); or any combination thereof.

In some embodiments, signals from detector 18 and encoder 42 may be transmitted to monitor 14. In the embodiment shown, monitor 14 may include a general-purpose microprocessor 48 connected to an internal bus 50. Microprocessor 48 may be adapted to execute software, which may include an operating system and one or more applications, as part of performing the functions described herein. Also connected to bus 50 may be a read-only memory (ROM) 52, a random access memory (RAM) 54, user inputs 56, display 20, data output 84, and speaker 22.

RAM 54 and ROM 52 are illustrated by way of example, and not limitation. Any suitable computer-readable media may be used in the system for data storage. Computer-readable media are capable of storing information that can be interpreted by microprocessor 48. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium that can be used to store the desired information and that can be accessed by components of the system.

In the embodiment shown, a time processing unit (TPU) 58 may provide timing control signals to light drive circuitry 60, which may control when emitter 16 is illuminated and multiplexed timing for Red LED 44 and IR LED 46. TPU 58 may also control the gating-in of signals from detector 18 through amplifier 62 and switching circuit 64. These signals are sampled at the proper time, depending upon which light source is illuminated. The received signal from detector 18 may be passed through amplifier 66, low pass filter 68, and analog-to-digital converter 70. The digital data may then be stored in a queued serial module (QSM) 72 (or buffer) for later downloading to RAM 54 as QSM 72 is filled. In some embodiments, there may be multiple separate parallel paths having components equivalent to amplifier 66, filter 68, and/or A/D converter 70 for multiple light wavelengths or spectra received. Any suitable combination of components (e.g., microprocessor 48, RAM 54, analog to digital converter 70, any other suitable component shown or not shown in FIG. 2) coupled by bus 50 or otherwise coupled (e.g., via an external bus), may be referred to as "processing equipment."

In some embodiments, microprocessor 48 may determine the patient's physiological parameters, such as $SpO_2$, pulse rate, and/or respiration information, using various algorithms and/or look-up tables based on the value of the received signals and/or data corresponding to the light received by detector 18. As is described herein, microprocessor 48 may generate respiration morphology signals and determine respiration information from a PPG signal.

Signals corresponding to information about patient 40, and particularly about the intensity of light emanating from a patient's tissue over time, may be transmitted from encoder 42 to decoder 74. These signals may include, for example, encoded information relating to patient characteristics. Decoder 74 may translate these signals to enable microprocessor 48 to determine the thresholds based at least in part on algorithms or look-up tables stored in ROM 52. In some embodiments, user inputs 56 may be used to enter information, select one or more options, provide a response, input settings, any other suitable inputting function, or any combination thereof. User inputs 56 may be used to enter information about the patient, such as age, weight, height, diagnosis, medications, treatments, and so forth. In some embodiments, display 20 may exhibit a list of values, which may generally apply to the patient, such as, for example, age ranges or medication families, which the user may select using user inputs 56.

Calibration device 80, which may be powered by monitor 14 via a communicative coupling 82, a battery, or by a conventional power source such as a wall outlet, may include any suitable signal calibration device. Calibration device 80 may be communicatively coupled to monitor 14 via communicative coupling 82, and/or may communicate wirelessly (not shown). In some embodiments, calibration device 80 is completely integrated within monitor 14. In some embodiments, calibration device 80 may include a manual input device (not shown) used by an operator to manually input reference signal measurements obtained from some other source (e.g., an external invasive or non-invasive physiological measurement system).

Data output 84 may provide for communications with other devices utilizing any suitable transmission medium, including wireless (e.g., WiFi, Bluetooth, etc.), wired (e.g., USB, Ethernet, etc.), or application-specific connections. Data output 84 may receive messages to be transmitted from microprocessor 48 via bus 50. Exemplary messages to be sent in an embodiment described herein may include samples of the PPG signal to be transmitted to an external device for determining respiration information.

The optical signal attenuated by the tissue of patient 40 can be degraded by noise, among other sources. One source of noise is ambient light that reaches the light detector. Another source of noise is electromagnetic coupling from other electronic instruments. Movement of the patient also introduces noise and affects the signal. For example, the contact between the detector and the skin, or the emitter and the skin, can be temporarily disrupted when movement causes either to move away from the skin. Also, because blood is a fluid, it responds differently than the surrounding tissue to inertial effects, which may result in momentary changes in volume at the point to which the oximeter probe is attached.

Noise (e.g., from patient movement) can degrade a sensor signal relied upon by a care provider, without the care provider's awareness. This is especially true if the monitoring of the patient is remote, the motion is too small to be observed, or the care provider is watching the instrument or other parts of the patient, and not the sensor site. Processing sensor signals (e.g., PPG signals) may involve operations that reduce the amount of noise present in the signals, control the amount of noise present in the signal, or otherwise identify noise components in order to prevent them from affecting measurements of physiological parameters derived from the sensor signals.

Figure 3:
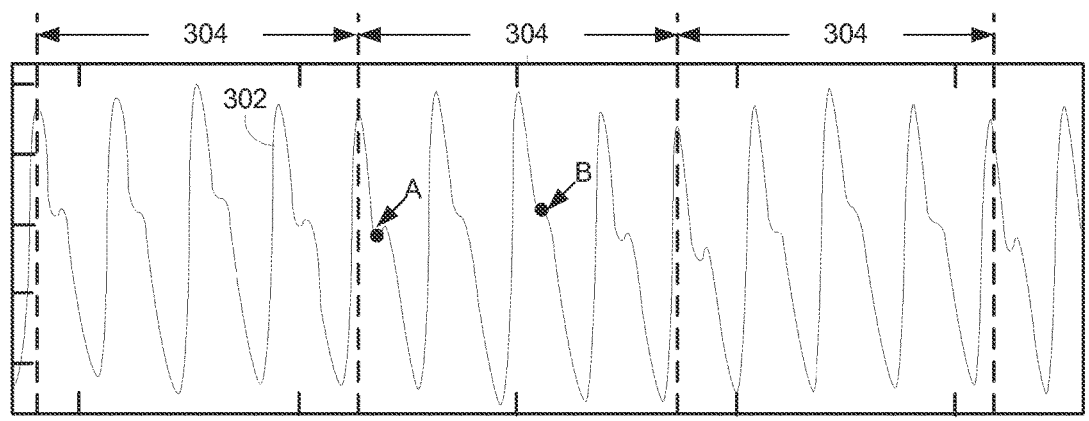
FIG. 3 shows an illustrative PPG signal that is modulated by respiration in accordance with some embodiments of the present disclosure.

FIG. 3 shows an illustrative PPG signal 302 that is modulated by respiration in accordance with some embodiments of the present disclosure. PPG signal 302 may be a periodic signal that is indicative of changes in pulsatile blood flow. Each cycle of PPG signal 302 may generally correspond to a pulse, such that a heart rate may be determined based on PPG signal 302. Each respiratory cycle 304 may correspond to a breath. The period of a respiratory cycle may typically be longer than the period of a pulsatile cycle, such that any changes in the pulsatile blood flow due to respiration occur over a number of pulsatile cycles. The volume of the pulsatile blood flow may also vary in a periodic manner based on respiration, resulting in modulations to the pulsatile blood flow such as amplitude modulation, frequency modulation, and baseline modulation. This modulation of PPG signal 302 due to respiration may result in changes to the morphology of PPG signal 302.

Figure 4:
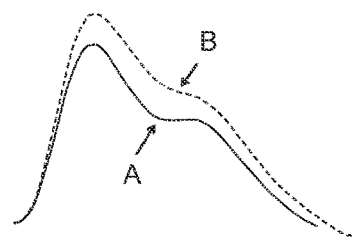
FIG. 4 shows a comparison of portions of the illustrative PPG signal of FIG. 3 in accordance with some embodiments of the present disclosure.

FIG. 4 shows a comparison of portions of the illustrative PPG signal 302 of FIG. 3 in accordance with some embodiments of the present disclosure. The signal portions compared in FIG. 4 may demonstrate differing morphology due to respiration modulation based on the relative location of the signal portions within a respiratory cycle 304. For example, a first pulse associated with the respiratory cycle may have a relatively low amplitude (indicative of amplitude and baseline modulation) as well as an obvious distinct dichrotic notch as indicated by point A. A second pulse may have a relatively high amplitude (indicative of amplitude and baseline modulation) as well as a dichrotic notch that has been washed out as depicted by point B. Frequency modulation may be evident based on the relative period of the first pulse and second pulse. Referring again to FIG. 3, by the end of the respiratory cycle 304 the pulse features may again be similar to the morphology of A. Although the impact of respiration modulation on the morphology of a particular PPG signal 302 has been described herein, it will be understood that respiration may have varied effects on the morphology of a PPG signal other than those depicted in FIGS. 3 and 4.

Figure 5:
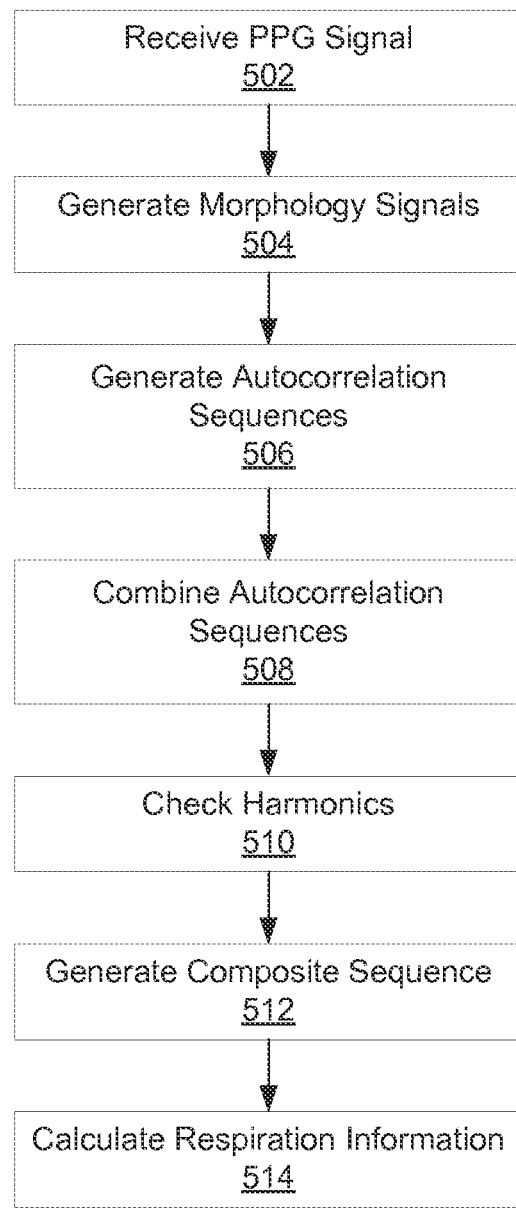
FIG. 5 shows illustrative steps for determining respiration information from a PPG signal in accordance with some embodiments of the present disclosure.

FIG. 5 shows illustrative steps for determining respiration information from a PPG signal in accordance with some embodiments of the present disclosure. Although exemplary steps are described herein, it will be understood that steps may be omitted and that any suitable additional steps may be added for determining respiration information. Although the steps described herein may be performed by any suitable device, in an exemplary embodiment, the steps may be performed by monitoring system 10. At step 502, monitoring system 10 may receive a PPG signal as described herein. Although the PPG signal may be processed in any suitable manner, in an embodiment, the PPG signal may be analyzed each 5 seconds, and for each 5 second analysis window, the most recent 45 seconds of the PPG signal may be analyzed.

At step 504, monitoring system 10 may generate one or more respiration morphology signals from the PPG signal. Although any number of respiration morphology signals may be generated from a PPG signal, in an embodiment, three respiration morphology signals may be generated. Although any respiration morphology signals may be generated, in an embodiment, a down signal, a delta of second derivative (DSD) signal, and a kurtosis signal may be generated. Although a respiration morphology signal may be generated in any suitable manner, in an embodiment, a respiration morphology signal may be generated based on calculating a series of morphology metrics based on a PPG signal. One or more morphology metrics may be calculated for each portion of the PPG signal (e.g., for each fiducial defined portion as described herein), a series of morphology metrics may be calculated over time, and the series of morphology metrics may be processed to generate one or more respiration morphology signals.

Figure 6:
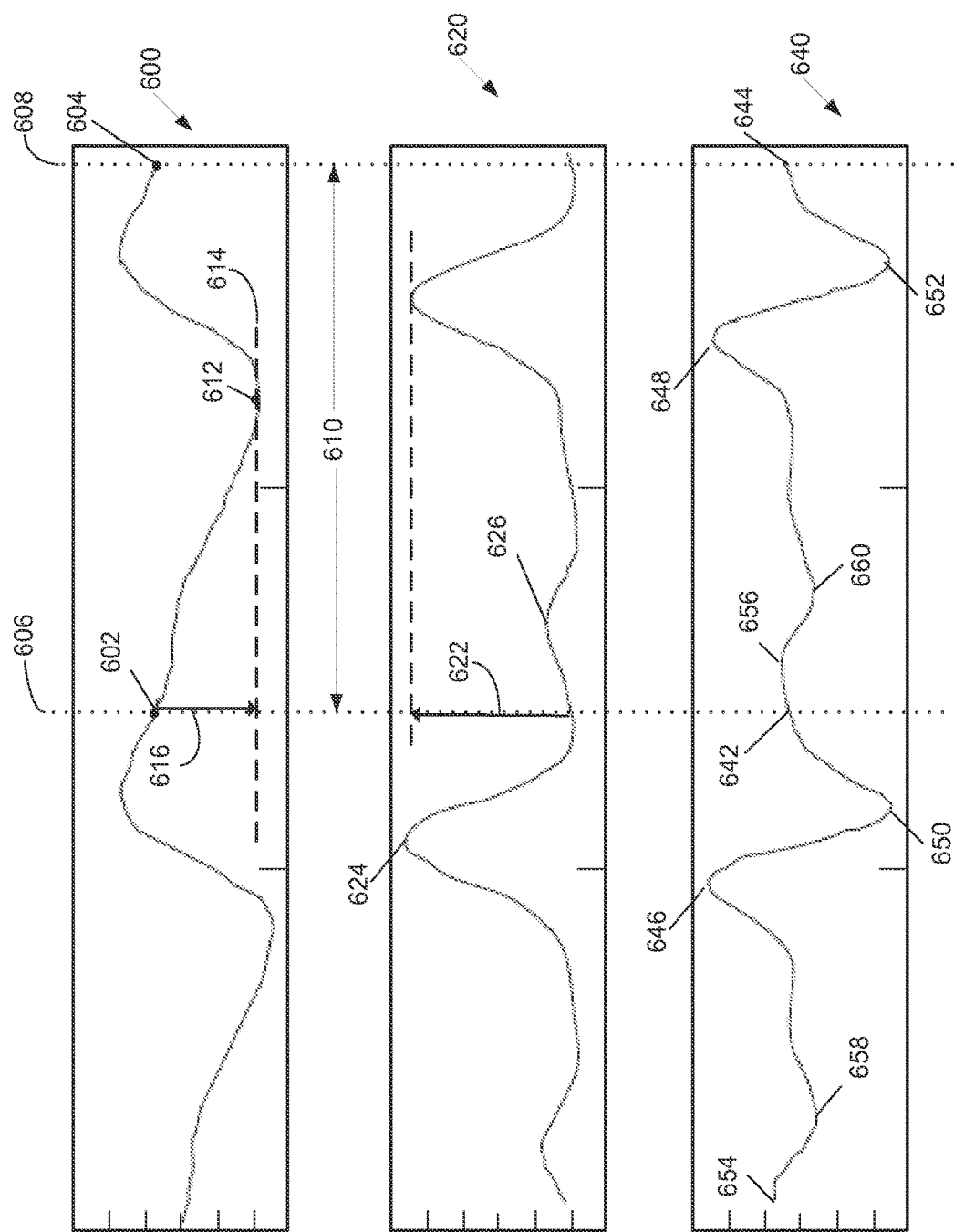
FIG. 6 shows an illustrative PPG signal, a first derivative of the PPG signal, and a second derivative of the PPG signal in accordance with some embodiments of the present disclosure.

FIG. 6 shows signals used for calculating morphology metrics from a received PPG signal. The abscissa of each plot of FIG. 6 may be represent time and the ordinate of each plot may represent magnitude. PPG signal 600 may be a received PPG signal, first derivative signal 620 may be a signal representing the first derivative of the PPG signal 600, and second derivative signal 640 may be a signal representing the second derivative of the PPG signal 600. As will be described below, these signals may be utilized to calculate morphology metrics that may be used as inputs to determine respiration information such as respiration rate. Although particular morphology metric determinations are set forth below, each of the morphology metric calculations may be modified in any suitable manner. Any of a plurality of morphology metrics may be utilized in combination to determine respiration information.

Exemplary fiducial points 602 and 604 are depicted for PPG signal 600, and fiducial lines 606 and 608 demonstrate the location of fiducial points 602 and 604 relative to first derivative signal 620 and second derivative signal 640. Fiducial points 602 and 604 may define a fiducial-defined portion 610 of PPG signal 600. The fiducial points 602 and 604 may define starting and ending points for determining morphology metrics as described herein, and the fiducial-defined portion 610 may define a relevant portion of data for determining morphology metrics as described herein. It will be understood that other starting points, ending points, and relative portions of data may be utilized to determine morphology metrics.

An exemplary morphology metric may be a down metric. The down metric is the difference between a first (e.g., fiducial) sample of a fiducial-defined portion (e.g., fiducial defined portion 610) of the PPG signal (e.g., PPG signal 600) and a minimum sample (e.g., minimum sample 612) of the fiducial-defined portion of the PPG signal. A down metric may also be calculated based on other points of a fiducial-defined portion. The down metric is indicative of physiological characteristics which are related to respiration, e.g., amplitude and baseline modulations of the PPG signal. In an exemplary embodiment fiducial point 602 defines the first location for calculation of a down metric for fiducial-defined portion 610. In the exemplary embodiment minimum sample of fiducial-defined portion 610 is minimum point 612, and is indicated by horizontal line 614. The down metric may be calculated by subtracting the value of minimum point 612 from the value of fiducial point 602, and is depicted as down metric 616.

Another exemplary morphology metric may be a kurtosis metric for a fiducial-defined portion. Kurtosis measures the peakedness of the first derivative 620 of the PPG signal. The peakedness is sensitive to both amplitude and period (frequency) changes, and may be utilized as an input to determine respiration information, such as respiration rate. Kurtosis may be calculated based on the following formulae:

$$D = \frac{1}{n}\sum_{i=1}^{n}(x'_i - \overline{x'})^2$$

-continued $$\text{Kurtosis} = \frac{1}{nD^2} \sum_{i=1}^{n} (x'_i - \overline{x'})^4$$

where:
$x_i'$=ith sample of $1^{st}$ derivative;
$\overline{x'}$=mean of 1st derivative of fiducial-defined portion;
n=set of all samples in the fiducial-defined portion Another exemplary morphology metric may be a delta of the second derivative (DSD) between consecutive fiducial-defined portions, e.g., at consecutive fiducial points. Measurement points 642 and 644 for a DSD calculation are depicted at fiducial points 602 and 604 as indicated by fiducial lines 606 and 608. The second derivative is indicative of the curvature of a signal. Changes in the curvature of the PPG signal are indicative of changes in internal pressure that occur during respiration, particularly changes near the peak of a pulse. By providing a metric of changes in curvature of the PPG signal, the DSD morphology metric may be utilized as an input to determine respiration information, such as respiration rate. The DSD metric may be calculated for each fiducial-defined portion by subtracting the second derivative of the next fiducial point from the second derivative of the current fiducial point.

Another exemplary morphology metric may be an up metric measuring the up stroke of the first derivative signal 620 of the PPG signal. The up stroke may be based on an initial starting sample (fiducial point) and a maximum sample for the fiducial-defined portion and is depicted as up metric 622 for a fiducial point corresponding to fiducial line 606. The up metric may be indicative of amplitude and baseline modulation of the PPG signal, which may be related to respiration information as described herein. Although an up metric is described herein with respect to the first derivate signal 620, it will be understood that an up metric may also be calculated for the PPG signal 600 and second derivative signal 640.

Another exemplary morphology metric may be a skew metric measuring the skewness of the original PPG signal 600 or first derivative 620. The skew metric is indicative of how tilted a signal is, and increases as the PPG signal is compressed (indicating frequency changes in respiration) or the amplitude is increased. The skewness metric is indicative of amplitude and frequency modulation of the PPG signal, which may be related to respiration information as described herein. Skewness may be calculated as follows:

$$g1 = \frac{m_3}{m_2^{3/2}} = \frac{\frac{1}{n}\sum_{i=1}^{n}(x_i - \overline{x})^3}{\left(\frac{1}{n}\sum_{i=1}^{n}(x_i - \overline{x})^2\right)^{3/2}}$$

where:
$x_i$=ith sample;
$\overline{x}$=mean of the samples of the fiducial-defined portion;
$m_3$=third moment;
$m_2$=second moment; and
n=total number of samples.

Another exemplary morphology metric may be a b/a ratio metric (i.e., b/a), which is based on the ratio between the a-peak and b-peak of the second derivative signal 640. PPG signal 600, first derivative signal 620, and second derivative signal 640 may include a number of peaks (e.g., four peaks corresponding to maxima and minima) which may be described as the a-peak, b-peak, c-peak, and d-peak, with the a-peak and c-peak generally corresponding to local maxima within a fiducial defined portion and the b-peak and d-peak generally corresponding to local minima within a fiducial defined portion. For example, the second derivative of the PPG signal may include four peaks: the a-peak, b-peak, c-peak, and d-peak. Each peak may be indicative of a respective systolic wave, i.e., the a-wave, b-wave, c-wave, and d-wave. On the depicted portion of the second derivative of the PPG signal 640, the a-peaks are indicated by points 646 and 648, the b-peaks by points 650 and 652, the c-peaks by points 654 and 656, and the d-peaks by points 658 and 660. The b/a ratio measures the ratio of the b-peak (e.g., 650 or 652) and the a-peak (e.g., 646 or 648). The b/a ratio metric may be indicative of the curvature of the PPG signal, which demonstrates frequency modulation based on respiration information such as respiration rate. The b/a ratio may also be calculated based on the a-peak and b-peak in higher order signals such as PPG signal and first derivative PPG signal 620.

Another exemplary morphology metric may be a c/a ratio (i.e., c/a), which is calculated from the a-peak and c-peak of a signal. For example, first derivate PPG signal 620 may have a c-peak 626 which corresponds to the maximum slope near the dichrotic notch of PPG signal 600, and an a-peak 624 which corresponds to the maximum slope of the PPG signal 600. The c/a ratio of the first derivative is indicative of frequency modulation of the PPG signal, which is related to respiration information such as respiration rate as described herein. A c/a ratio may be calculated in a similar manner for PPG signal 600 and second derivative signal 640.

Another exemplary morphology metric may be a i_b metric measuring the time between two consecutive local minimum (b) locations 650 and 652 in the second derivative 640. The i_b metric is indicative of frequency modulation of the PPG signal, which is related to respiration information such as respiration rate as described herein. The i_b metric may also be calculated for PPG signal 600 or first derivative signal 620.

Another exemplary morphology metric may be a peak amplitude metric measuring the amplitude of the peak of the original PPG signal 600 or of the higher order derivatives 620 and 640. The peak amplitude metric is indicative of amplitude modulation of the PPG signal, which is related to respiration information such as respiration rate as described herein.

Another exemplary morphology metric may be a center of gravity metric measuring the center of gravity of a fiducial-defined portion from the PPG signal 600 in either or both of the x and y coordinates. The center of gravity is calculated as follows:

Center of gravity $(x) = \Sigma(x_i * y_i)/\Sigma y_i$

Center of gravity $(y) = \Sigma(x_i * y_i)/\Sigma x_i$

The center of gravity metric of the x coordinate for a fiducial-defined portion is indicative of frequency modulation of the PPG signal, which is related to respiration information such as respiration rate as described herein. The center of gravity metric of the y coordinate for a fiducial-defined portion is indicative of amplitude modulation of the PPG signal, which is related to respiration information such as respiration rate as described herein.

Another exemplary morphology metric is an area metric measuring the total area under the curve for a fiducial-defined portion of the PPG signal 600. The area metric is indicative of frequency and amplitude modulation of the PPG signal, which is related to respiration information such as respiration rate as described herein.

Although a number of morphology metrics have been described herein, it will be understood that other morphology metrics may be calculated from PPG signal 600, first derivative signal 620, second derivative signal 640, and any other order of the PPG signal. It will also be understood that any of the morphology metrics described above may be modified to capture aspects of respiration information or other physiological information that may be determined from a PPG signal.

Referring again to FIG. 5, at step 504, respiration morphology signals may be calculated for each morphology metric (e.g., down, kurtosis, and DSD). In some embodiments, each series of morphology metric values may be further processed in any suitable manner to generate the respiration morphology signals. Although any suitable processing operations may be performed for each series of morphology metric values, in an exemplary embodiment, each series of morphology metric values may be filtered (e.g., based on frequencies associated with respiration) and interpolated to generate the plurality of respiration morphology signals. In an exemplary embodiment where a series of morphology metric values for the down metric, kurtosis metric, and DSD metric are generated for the received PPG signal, the resulting respiration morphology signals may be a down morphology signal, a kurtosis morphology signal, and a DSD morphology signal.

At step 506, monitoring system 10 may generate an autocorrelation sequence for each of the respiration morphology signals, e.g., the down metric signal, kurtosis metric signal, and DSD metric signal, respectively. Autocorrelation is the cross-correlation of a signal with itself, and to the extent that the underlying signal includes regular or repeating patterns, the peaks of the autocorrelation may correspond to periodic components of the underlying signal. The autocorrelations of the respiration morphology signals may be utilized to determine respiration information such as respiration rate as described herein. However, a single autocorrelation sequence corresponding to a single respiration morphology respiration signal may not provide sufficient information to determine the respiration information with a desired accuracy or certainty in all instances. Accordingly, a plurality of autocorrelation sequences corresponding to respective respiration morphology signals may be utilized to determine respiration information. The formula for the autocorrelation is the following:

$$R_{xx}(m) = \Sigma_{n \in S} x(n) x(n-m), \text{ for } m=-M, \ldots, M$$

where:
S=the signal support of the finite segment;
M=the maximum lag computed for the autocorrelation.

Once an autocorrelation sequence is generated for each of the respiration morphology signals, the autocorrelation sequences may be combined at step 508 to generate a combined autocorrelation sequence for the most recent data window. Although it will be understood that the combined autocorrelation sequence may be generated in any suitable manner, in some embodiments, weighting factors may be determined for each of the autocorrelation sequences and the weighted autocorrelation sequences may be combined to generate the combined autocorrelation sequence. Although any suitable weighting factor may be calculated based on any suitable parameters, in an exemplary embodiment the weighting factor may be based on the regularity or consistency of each autocorrelation sequence. The combined autocorrelation sequence may then be generated according to the following:

$$\text{Combined Sequence} = \frac{(w_{C-D} * S_D + w_{C-K} * S_K + w_{C-DSD} * S_{DSD})}{(w_{C-D} + w_{C-K} + w_{C-DSD})}$$

where:
$w_{C-D}$=combination weight for down metric sequence;
$w_{C-K}$=combination weight for kurtosis sequence;
$w_{C-DSD}$=combination weight for DSD sequence;
$S_D$=filtered down sequence;
$S_K$=filtered kurtosis sequence; and
$S_{DSD}$=filtered DSD sequence.

Processing may then continue to step 510. At step 510, a harmonic check may be performed for the combined autocorrelation sequence to determine whether to use the current autocorrelation sequence to determine respiration information. Although the harmonic check is described herein as being performed on the combined autocorrelation sequence, it will be understood that the harmonic check could be performed independently for some or all of the autocorrelation sequences described herein. For example, in some embodiments, the harmonic check may be performed for each of the autocorrelation sequences generated from each of the respiration morphology signals, and an autocorrelation sequence may be generated only from the autocorrelation sequences that pass the harmonic check. In some embodiments, the harmonic check may be performed for the composite autocorrelation sequence described with respect to step 512, and the composite sequence may be used to calculate respiration information only if the harmonic check is passed.

For autocorrelation sequences that do not include harmonics, it is typically expected that each subsequent peak in the autocorrelation sequence will be smaller than the previous peak. For example, the peak heights may be expected to decay with increasing time lag. For autocorrelation sequences that include strong harmonics, a pattern of "small-large" peaks may be present.

Figure 7:
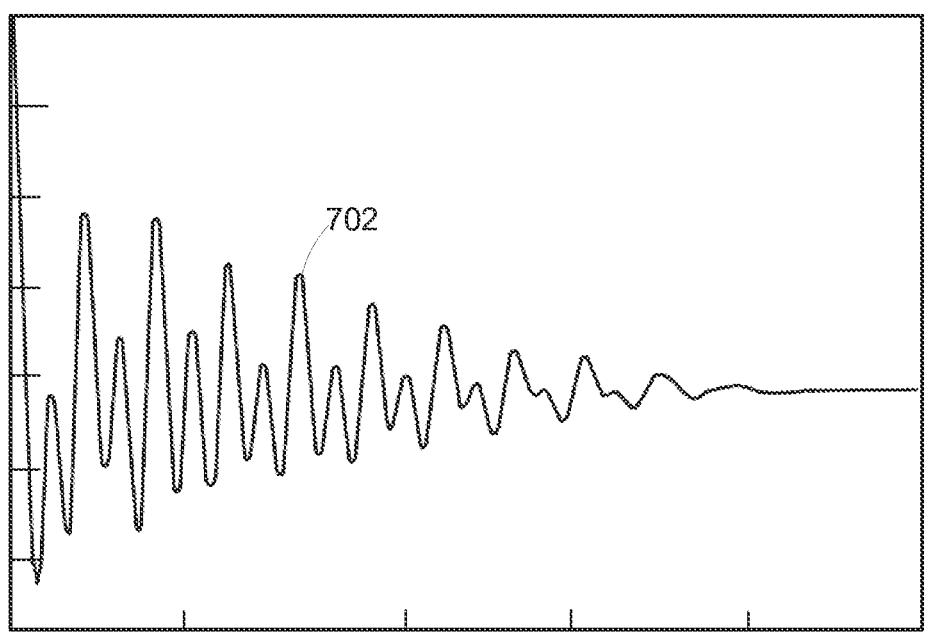
FIG. 7 shows an illustrative autocorrelation signal in accordance with some embodiments of the present disclosure.

FIG. 7 shows an illustrative combined autocorrelation sequence that includes harmonics in accordance with some embodiments of the present disclosure. Combined autocorrelation sequence 702 includes local maxima and minima, some of which may be indicative of respiration information and some of which may be indicative of harmonics. In the exemplary embodiment depicted in FIG. 7, the larger peaks may be indicative of respiration rate, while the smaller peaks may be indicative of a harmonic of the respiration rate (i.e., at 2 times the respiration rate). As shown, the peaks form a pattern of "small-large" peaks. It may be desirable to determine the strength of the harmonic contribution to the combined autocorrelation sequence to determine whether harmonics are likely to interfere with the proper determination of respiration rate.

Figure 8:
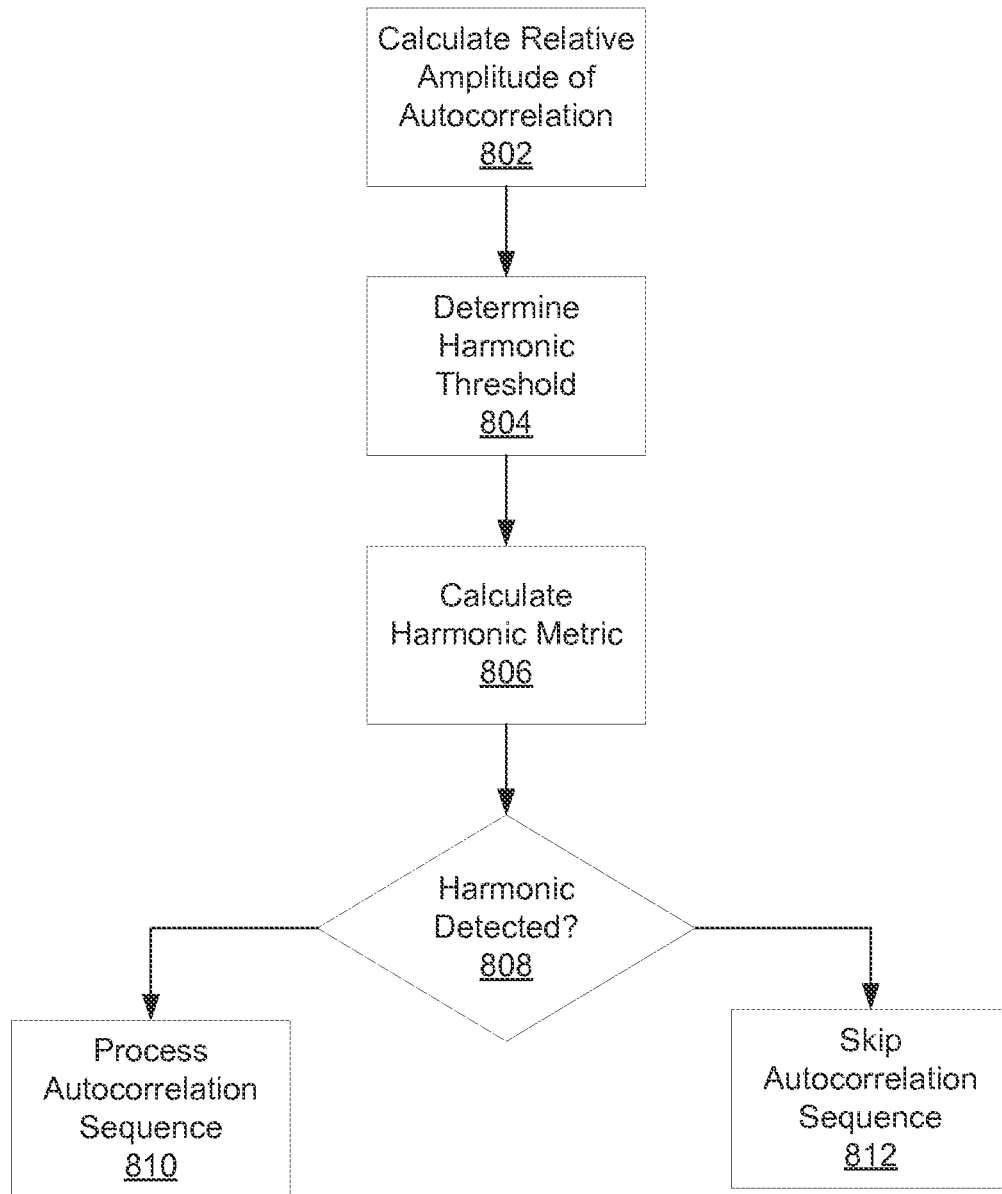
FIG. 8 shows illustrative steps for performing a harmonic check in accordance with some embodiments of the present disclosure.

FIG. 8 shows illustrative steps for performing a harmonic check in accordance with some embodiments of the present disclosure. Although a particular sequence of steps is described herein, it will be understood that steps may be modified or removed, and additional steps may be added, in accordance with the present disclosure. Harmonics may appear in a respiration signal for a number of reasons. In some circumstances a patient's pulse rate may be an integer multiple of the patient's respiration rate, which may result in a strong coupling between a sub-harmonic of the pulse rate and a harmonic of the respiration rate. For example, if the pulse rate is 4 times the respiration rate (e.g., pulse rate of 60 beats per minute and respiration rate of 15 breaths per minute), the first harmonic of the respiration rate at 2 times the respiration rate (e.g., 30 breaths per minute or 0.5 Hz) may be reinforced by the first sub-harmonic of the heart rate at ½ times the pulse rate (e.g., 30 beats per minute or 0.5 Hz). As another non-limiting example, a patient that is undergoing mechanical breathing assistance (ventilation) may show strong and consistent energy at harmonics of the respiration rate.

At step 802, the relative amplitude of each local maxima in the autocorrelation sequence may be calculated. Although calculation of the relative amplitude of the local maxima are described as being calculated herein, it will be understood that any suitable values may be calculated from the autocorrelation sequence in accordance with the present disclosure. In some embodiments, the local maxima may be calculated as patterns in the local maxima and may be indicative of the presence of strong harmonics. For example, in the autocorrelation sequence depicted in FIG. 7, a pattern indicative of harmonics may be the repeating pattern of a small peak followed by a big peak. In some embodiments, the local maxima associated with each peak may be calculated based on the maxima of the peak minus the average of the prior and subsequent adjacent minimas:

$$\text{amplitude}(k) = \text{maxima}(k) - \frac{\text{minima}(k) + \text{minima}(k-1)}{2}$$

where:
amplitude (k)=relative amplitude for the kth peak;
maxima (k)=local maxima of the kth peak;
minima (k)=minima for the valley subsequent to the kth peak; and
minima(k−1)=minima for the valley preceding the kth peak.

At step 804, a threshold may be determined for comparison with the relative amplitude values calculated in step 802. Although the threshold may be based on any suitable criteria, in some embodiments, the threshold may be based on whether harmonics were recently identified. Although the recent history of harmonics may be analyzed in any suitable manner, in some embodiments, if analysis of the most recently received data indicated the presence of harmonics, a liberal threshold may be set, while if analysis of the most recently received data indicated the presence of strong harmonics, a conservative threshold may be set. A more liberal threshold may be used when harmonics were recently identified because it may be assumed that more harmonics are likely to occur. For example, if harmonics were identified in the previous analysis window, then a liberal threshold may be set. Otherwise, a conservative threshold may be set. In an embodiment, the liberal threshold may be 0.9 while the conservative threshold may be 0.35.

At step 806 a harmonic metric may be calculated. Although a harmonic metric may be calculated in any suitable manner, in some embodiments, a harmonic metric may be based on the number of peaks having an amplitude that exceed the previous peak multiplied by threshold value. In an embodiment, the harmonic metric may be calculated as follows:

$$HMetric = \frac{\sum_{k=1}^{N-1} \text{amplitude}(k) < \text{threshold} * \text{amplitude}(k+1)}{\left(\frac{N}{2}\right)}$$

where:
HMetric=Harmonic metric for the autocorrelation sequence;
amplitude (k)=relative amplitude for the kth peak;
amplitude (k+1)=relative amplitude for the k+1th peak;
N=number of peaks in the autocorrelation sequence; and
k is incremented by 2 for each iteration.

At decision block 808 it may be determined whether harmonics are detected for the current autocorrelation sequence. Although the determination of the presence of harmonics may be performed in any suitable manner, in an embodiment, the evaluation may be based on the harmonic metric, a history of harmonics in recent autocorrelation sequences, and additional statistics related to the current autocorrelation sequence. In some embodiments, it may be determined if there are a threshold number of peaks (e.g., 3 peaks) of the autocorrelation sequence that have a sufficient relative amplitude (e.g., 0.1), and if so, four tests may be performed to determine if harmonics are present. If any of the tests indicate the presence of harmonics, processing may continue to step 812, while if none of the tests indicate the presence of strong harmonics, processing may continue to step 810. In some embodiments, the tests may be configured to detect strong harmonics.

An exemplary first harmonic test may be based on a recent history of harmonics and the harmonic metric value. For example, if the previous autocorrelation sequence included harmonics and the harmonic metric for the current autocorrelation sequence exceeds 0.5 (i.e., indicating that the relative amplitude value of more than 50% of the peaks of the autocorrelation sequence exceeded the relative amplitude value of the previous peak by more than the threshold), a harmonic may be detected.

An exemplary second harmonic test may be based on statistics for the current autocorrelation sequence. For example, if, for all peaks of the autocorrelation sequence, the relative amplitude the peaks is less than one-half of the relative amplitude of the subsequent peak, a harmonic may be detected.

An exemplary third harmonic test may be based on the harmonic metric value and statistics for the current autocorrelation sequence. For example, if the harmonic metric value for the current autocorrelation sequence exceeds 0.5 (i.e., indicating that the relative amplitude value of more than 50% of the peaks of the autocorrelation sequence exceeded the relative amplitude value of the previous peak by more than the threshold) and there are at least six peaks in the current autocorrelation sequence, a harmonic may be detected.

An exemplary fourth harmonic test may be based on a recent history of harmonics, the harmonic metric, and statistics for the current autocorrelation sequence. For example, if the respiration rate associated with the current autocorrelation sequence is approximately 2 times the respiration rate associated with the previous autocorrelation sequence, and if the amplitude of the second peak in the autocorrelation sequence is greater than the amplitude of the first, and if the harmonic metric is greater than 0.2, then a harmonic may be detected.

If processing continues to step 810 (e.g., strong harmonics were not identified for the current autocorrelation sequence), an indication may be provided that harmonics were not detected for the current autocorrelation sequence and processing to determine respiration information may continue normally.

If processing continues to step 812 (e.g., strong harmonics were identified for the current autocorrelation sequence), an indication may be provided that strong harmonics were detected for the current autocorrelation sequence and that the respiration information should not be calculated for the current autocorrelation sequence. When a new analysis window is selected every 5 seconds and the current autocorrelation sequence is not processed, then an age metric (e.g., composite segment age) will be increased by 5 seconds. The presence of persistent strong harmonics (e.g., due to mechanical breathing assistance) may cause the system to hold the previously calculated value for up to a time limit (e.g., 30 seconds, 1 minute, 2 minutes, or any other suitable time limit), and then drop out. For free breathing subjects, strong harmonics are typically short-lived events and it is unlikely that drop outs will occur due to harmonics. Therefore, under most circumstances, the system will hold the previously reported respiration information for a short while to coast over occurrences of harmonics. It will be understood that step 812 is merely exemplary and any suitable processing may be performed when a harmonic is detected. For example, in some embodiments, a different processing technique may be used to determine respiration information or any other suitable modifications to subsequent processing steps may be made when harmonics are present.

Referring again to FIG. 5, at step 512, monitoring system 10 may generate a composite autocorrelation sequence based on the combined autocorrelation sequence and the previously-determined composite autocorrelation sequence. Although a composite autocorrelation sequence may be generated in any suitable manner, in an exemplary embodiment, the composite autocorrelation sequence may be generated based on the steps depicted in FIG. 9.

Figure 9:
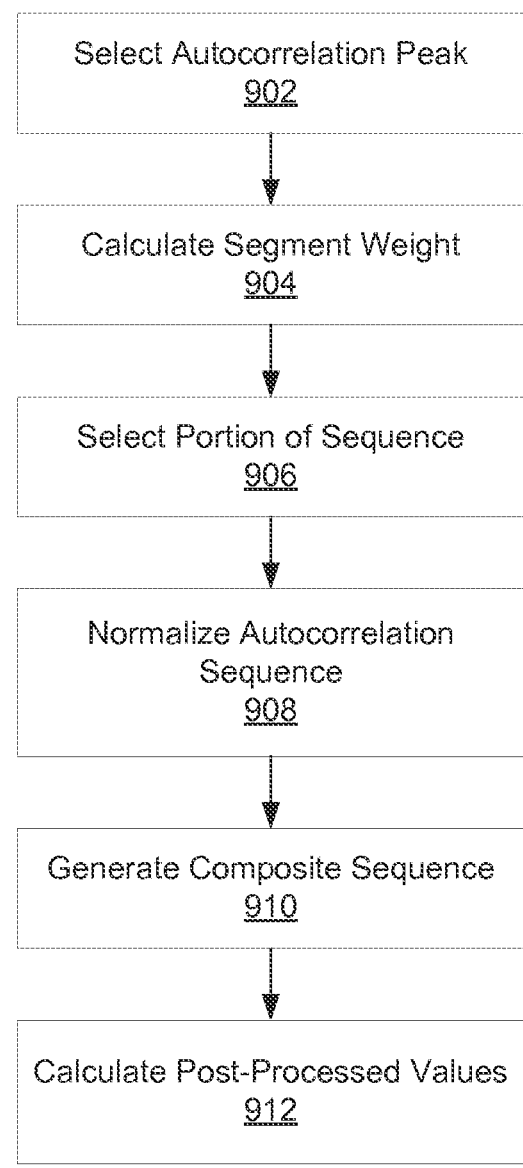
FIG. 9 shows an illustrative steps for generating a composite autocorrelation sequence in accordance with some embodiments of the present disclosure.

FIG. 9 shows illustrative steps for generating a composite autocorrelation sequence in accordance with some embodiments of the present disclosure. Although a particular sequence of steps is described herein, it will be understood that steps may be modified or removed, and additional steps may be added, in accordance with the present disclosure.

Figure 10:
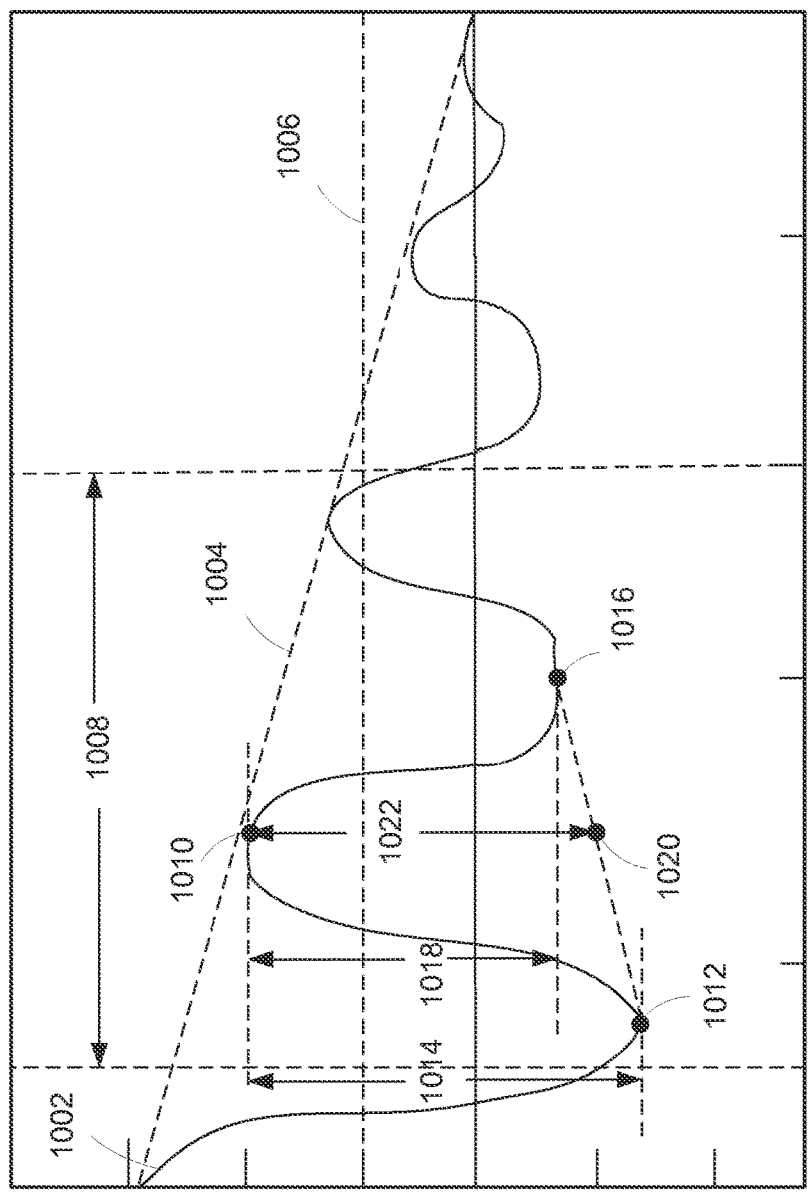
FIG. 10 shows an illustrative combined autocorrelation sequence in accordance with some embodiments of the present disclosure.

At step 902, a peak corresponding to respiration information may be selected from the combined autocorrelation sequence. FIG. 10 shows an illustrative combined autocorrelation sequence 1002 that may be directly analyzed to determine respiration information. Sequence 1002 is a generally noise-free idealized combined autocorrelation sequence for purposes of illustrating how a peak may be selected. The exemplary combined autocorrelation sequence 1002 may have a series of peaks that appear at regular intervals and (e.g., in the absence of harmonics) decrease in magnitude with increasing time lag. Line 1004 may be indicative of a rate of decay of the combined autocorrelation sequence 1002 and may define an expected autocorrelation envelope. The peaks of the combined autocorrelation sequence 1002 may roughly align with the rate of decay, which may be indicative of a signal from which respiration information may be accurately determined.

In some embodiments, a threshold may be set for the combined autocorrelation sequence such that peaks corresponding to harmonics and low magnitude peaks of signals that are irregular or non-periodic are ignored for determining respiration information. An exemplary threshold is depicted as threshold 1006 in FIG. 10. The threshold may be compared to one or more peak amplitudes. The peak amplitude may be determined based on the difference between the peak amplitude and the average of the prior and subsequent adjacent minimas as described above, or may be determined in any other suitable manner.

In some embodiments, a relevant range of interest may be determined or identified, e.g., based on the time scale of the combined autocorrelation sequence. The peaks of the combined autocorrelation sequence may correspond to instances where the underlying signal (e.g., a respiration morphology signal) has been translated in time and is similar to itself, which may demonstrate a periodic or regular signal. Thus the time between peaks that are representative of the respiration information may be equivalent to the period of the respiration, which may be utilized to determine respiration rate (e.g., the frequency of respiration). In an embodiment, a range of interest may be set to correspond to a respiration rate, such as from 4 to 40 breaths per minute. An exemplary range of interest is depicted as range of interest 1008 in FIG. 10. It will be understood that the range of interest may be set in any suitable manner. For example, in another embodiment the range of interest may be based upon a recent history of reported respiration rate values.

In an embodiment, a peak associated with respiration information such as respiration rate may be selected. It will be understood that selecting the peak may be performed in any suitable manner, such as selecting the first peak to the right of the vertical axis or a maximum peak value, e.g., peak 1010 in FIG. 10. In another exemplary embodiment, selecting the peak may be based on parameters such as a threshold and a range of interest. For example, peak 1010 in FIG. 10 may be the first peak that exceeds threshold 1006 and is within range of interest 1008. Selecting a peak within a range of interest may be performed in any suitable manner, such as selecting the first peak within the range of interest or selecting the peak with the largest amplitude.

In another embodiment, analysis of the peaks may be based on the peak to trough amplitude of the peak. The peak to trough amplitude may be based on any suitable points. In an embodiment, a peak to trough amplitude may be based on a selected peak and a preceding trough, as is depicted by amplitude 1014 between peak 1010 and trough 1012 in FIG. 10. In another embodiment, a peak to trough amplitude may be based on a selected peak and a subsequent trough, as is depicted by amplitude 1018 between peak 1010 and trough 1016 in FIG. 10. In another embodiment, a peak to trough amplitude may be based on a selected peak and an average or midpoint trough associated with the peak, as is depicted by amplitude 1022 between peak 1010 and midpoint trough 1020 in FIG. 10. Once the peak to trough amplitude is determined for the peak, selecting a peak corresponding to respiration information may be performed in any suitable manner, such as comparing the amplitude of each peak within a range of interest to a threshold, and selecting a peak based on amplitude and/or relative position.

Figure 11:
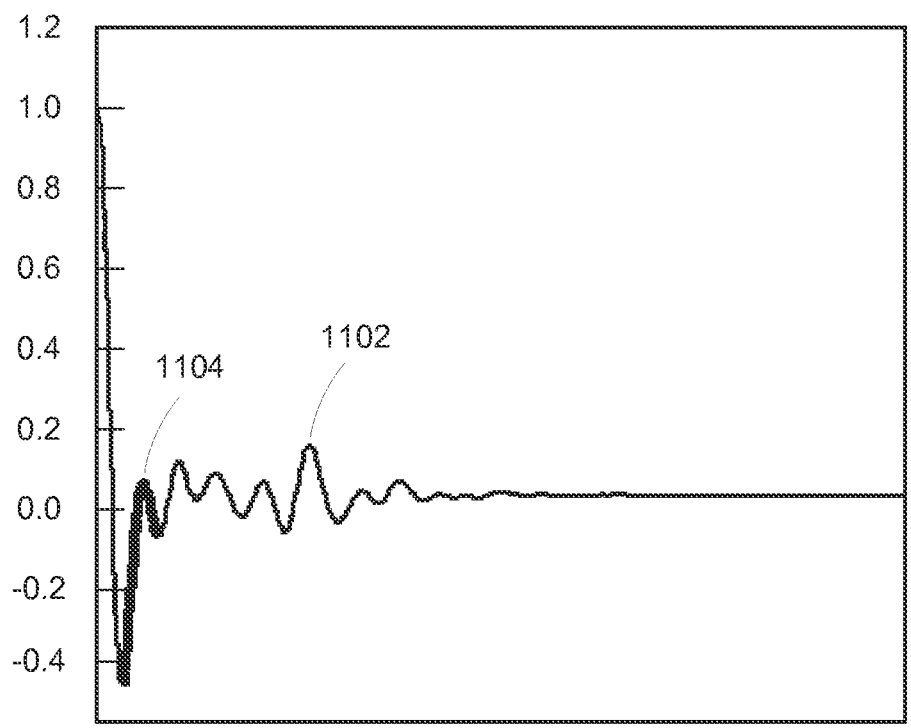
FIG. 11 shows an illustrative combined autocorrelation sequence in accordance with some embodiments of the present disclosure.

FIG. 11 shows an illustrative combined autocorrelation sequence 1102 that may be generated from an actual PPG signal. Noise in the PPG signal causes variability in the amplitudes of the peaks in sequence 1102, but sequence 1102 does not include the "small-large" peak pattern indicative of harmonics. Using the foregoing peak selection techniques, peak 1104, which comprises the bolded section of sequence 1102, may be selected. Once a peak of a combined autocorrelation sequence is selected, processing may continue at step 904 of FIG. 9.

Referring again to FIG. 9, at step 904, a segment weight may be calculated for the combined autocorrelation sequence. The segment weight may determine the relative contribution of the selected segment of the combined autocorrelation sequence (i.e., associated with the selected peak) to the final composite sequence that is used to calculate respiration information. Although a segment weight may be determined in any suitable manner, in an embodiment, the segment weight may be based on the amplitude of the selected peak of the combined autocorrelation sequence. Although the amplitude of the selected peak may be used to determine the segment weight in any suitable manner, in an embodiment, a constant may be subtracted from the height of the autocorrelation sequence (e.g., height of selected segment minus 0.1), with the resulting segment weight having maximum and minimum limits (e.g., a maximum of 1.0 and a minimum 0.075). In some embodiments the segment weight may be further down-weighted if the current combined autocorrelation sequence is based on a partial new data segment. Although the segment weight value may be down-weighted in any suitable manner, in an embodiment, if the combined autocorrelation sequence represents less than 2 seconds of new data (e.g., of a possible 5 seconds of new data), the calculated segment weight value may be multiplied by 0.6. In some embodiments, preprocessing of new data may cause one or more portions of the new data to be removed, for example, due to noise. Therefore, while 5 seconds of new data may be acquired, less than 5 seconds of new data may be used when generating the combined autocorrelation sequence. Processing may then continue to step 906.

At step 906, a segment of the combined autocorrelation may be selected and isolated based on the selected peak. Although any suitable portion of the combined autocorrelation sequence associated with the peak may be selected and isolated, in an embodiment, a portion of the autocorrelation sequence that begins with the minima that precedes the selected autocorrelation peak and that ends with the minima subsequent to the selected autocorrelation peak may be selected. Although the remainder of the combined autocorrelation sequence may be processed in any suitable manner, in an embodiment, the remainder of the combined autocorrelation sequence may then be padded with zeros (i.e., the remainder of the combined autocorrelation sequence may be discarded and replaced with zero values). The selected segment (e.g., the selected portion and padded portion) may then be further processed at step 908.

At step 908, the selected segment of the combined autocorrelation sequence may be normalized. Although the selected segment may be normalized in any suitable manner, in an embodiment, the selected segment may be normalized based on the maximum minima-to-maxima value for the selected segment. Processing may then continue to step 910.

At step 910, a composite sequence may be generated based on the normalized segment of the autocorrelation sequence. Although the composite sequence may be generated in any suitable manner, in an embodiment, the composite sequence may be generated based on the current normalized segment, the composite segment that was generated for the most recent window of received data, and the segment weight value. For each point in the normalized sequence and an associated point in the previous composite segment (i.e., for points having the same lag value), a composite segment value may be calculated as follows:

$$\text{composite}(k)=\text{segwt}*\text{normseg}(k)+(1-\text{segwt})*\text{composite}'(k)$$

where:
k=lag value;
composite(k)=value for the kth point of the composite segment;
composite'(k)=value for the kth point of the previous composite segment;
normseg(k)=value for the kth point of the current normalized segment; and
segwt=segment weight value.

Figure 12:
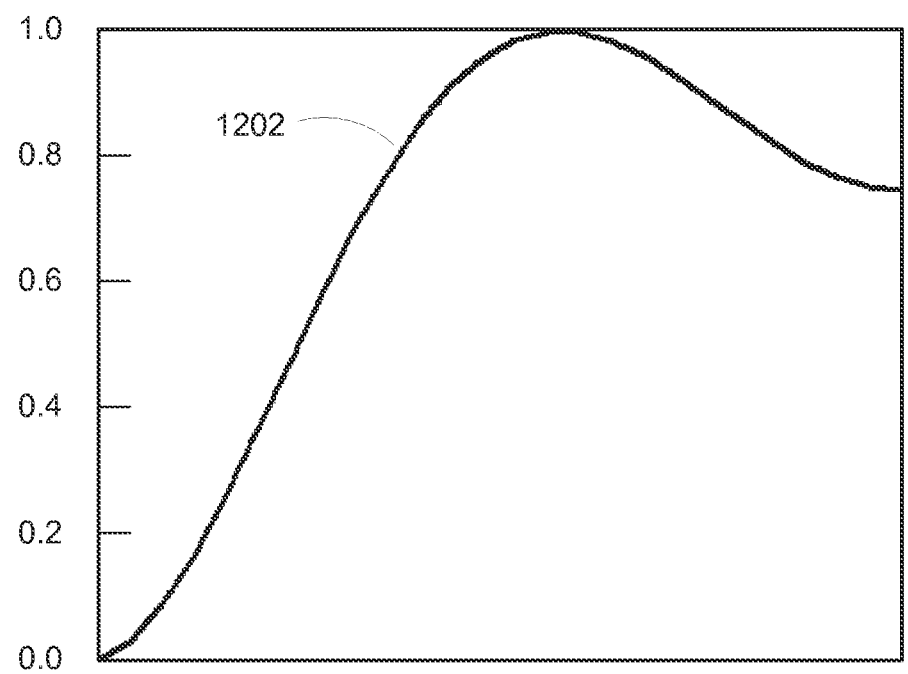
FIG. 12 shows an illustrative normalized segment that may be generated in accordance with some embodiments of the present disclosure.
Figure 13:
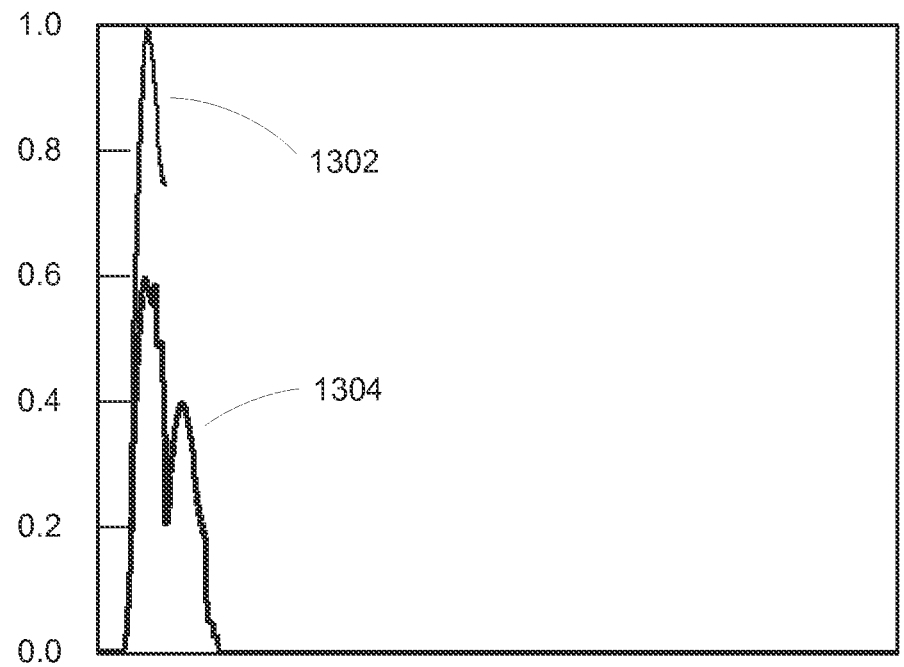
FIG. 13 shows illustrative signal segments that may be generated in accordance with some embodiments of the present disclosure.

FIG. 13 shows an illustrative normalized segment 1302 and an exemplary composite segment 1304 that may be combined to generate a new composite segment. In some embodiments normalized segment 1302 may correspond to normalized segment 1202 of FIG. 12 and composite segment 1304 may correspond to the composite segment generated using the previous window of received data.

Once the composite segment is calculated, processing may continue to step 912, where post-processor values may be calculated for use in later processing steps. Although any suitable post-processing values may be calculated, in an embodiment, a composite segment age and an average segment height may be calculated. The composite segment age may quantify the total filter response time for the current composite segment. In some embodiments, a composite segment age value may be used to prevent posting of respiration information if the age exceeds a threshold (i.e., if the respiration information would be calculated largely from old data). For example, the composite segment age may be passed to a postprocessor and may be used by the postprocessor to prevent posting respiration rate to a user if the age is greater than a threshold (e.g., 120 seconds). Although a composite segment age may be calculated in any suitable manner, in an embodiment the composite segment age may be calculated as follows:

$$\text{composite\_age}=\text{segwt}*\text{current\_age}+(1-\text{segwt})*(\text{composite\_age}+5)'$$

where:
composite_age=composite age for the current composite segment in seconds;
composite_age'=composite age for the previous composite segment in seconds;
current_age=age of the current normalized segment in seconds; and
segwt=segment weight value.

The average segment height may be considered a confidence metric associated with the current composite segment. In an embodiment, the average segment height may be used to determine if there is sufficient confidence to report a respiration information value calculated from the current composite segment to a user. For example, the average segment height may be passed to a postprocessor and may be used to by the postprocessor to prevent posting respiration rate to a user if the height is less than a threshold. Although the average segment height age may be calculated in any suitable manner, in an embodiment the average segment height may be calculated as follows:

$$\text{average\_height}=\text{segwt}*\text{current\_height}+(1-\text{segwt})*\text{average\_height}'$$

where:
average_height=average segment height for the current composite segment;
average_height'=average segment height for the previous composite segment;
current_height=height of the current segment before normalization; and
segwt=segment weight value.

Once all of the post-processor values are calculated, processing may return to step 514 of FIG. 5. At step 514, monitoring system 10 may determine respiration information from the composite sequence. Although any suitable respiration information may be determined, in an embodiment the respiration information may be respiration rate. Although respiration rate may be determined in any suitable manner, in an embodiment the respiration information may be based on a first maxima of the composite segment that exceeds a threshold. The threshold may be fixed, variable, or may be set in any other suitable manner. In an embodiment, a lower threshold may be more likely to select a high respiration rate, and thus, the threshold may be variable based on a likelihood that the respiration rate has a relatively high value. Although a threshold may be determined in any suitable manner, in an embodiment the threshold may be determined by a neural network that assigns a value based on the likelihood that the respiration rate is high. The threshold may then be the greater of a fixed value or a value based on the output of the neural network. For example, the threshold may be calculated as follows:

$$\text{threshold} = \max(0.45, (1 - NN\_\text{output})^2)$$

where:
threshold=threshold for identifying maxima associated with respiration rate;
NN_output=output of neural network; and
max(x,y)=select the maximum of the first and second value.

In some embodiments, the composite segment may be processed prior to being compared to the threshold. Although the composite segment may be processed in any suitable manner, in an embodiment, the composite segment may be low-pass filtered with a first order Butterworth filter having a cutoff frequency of approximately 45 breaths per minute. In some embodiments, the filtering may be configured to remove spurious peaks that are outside the frequency range of interest for respiration rate. The filtering may also be configured to remove any artifacts associated with combining the normalized segment with the previous composite segment. For example, artifacts may be introduced when the normalized segment and the previous composite segments are of different lengths. In some embodiments, the cutoff frequency of the filter or filter characteristics may be determined as a function of pulse rate, or a preliminary respiration rate estimate. For example, when pulse rate is high, the cutoff frequency may be set to a higher value. When pulse rate is low, the cutoff frequency may be set to a lower value. In both cases, the cutoff frequency may be set to a value that is lower than the pulse rate. The composite segment may be filtered twice, once in each direction, to achieve zero phase change.

Figure 14:
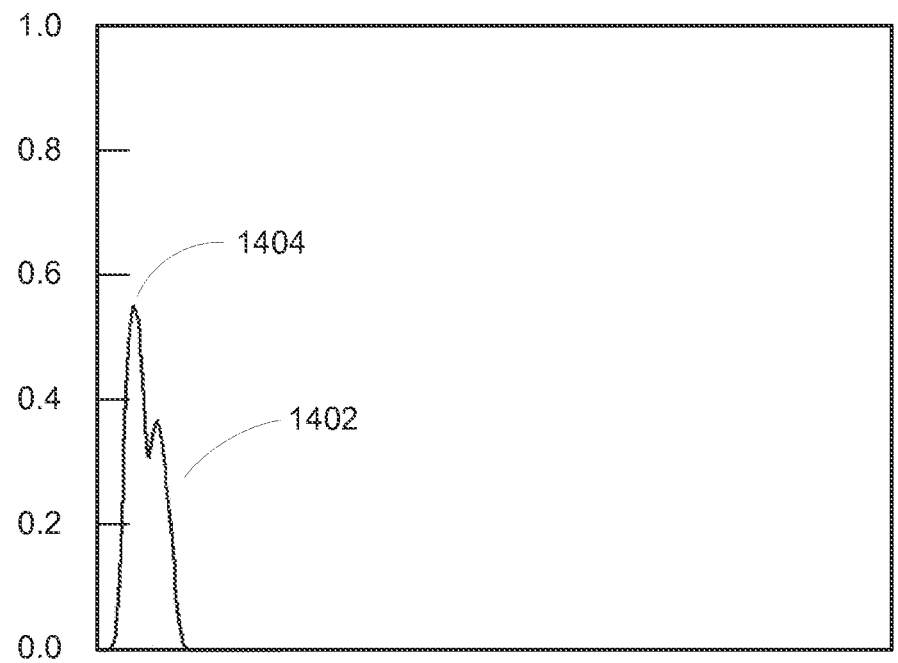
FIG. 14 shows an illustrative processed composite signal that may be generated in accordance with some embodiments of the present disclosure.

FIG. 14 shows an illustrative processed composite signal 1402. In some embodiments, processed composite signal 1402 may be generated by combining and filtering normalized segment 1302 and composite segment 1304 of FIG. 13. Normalized segment 1302 includes a single peak and composite segment 1304 includes two main peaks with a medium depth trough therebetween. The peak of normalized segment 1302 is generally aligned with the first peak of composite segment 1304. The second peak of composite segment 1304 may be due to noise or may be associated with an earlier different respiration rate. By combining and filtering these segments, the first peak of composite segment 1304 is generally maintained and the second peak of segment 1304 is attenuated as shown by processed composite signal 1402.

The respiration rate may be determined based on the local maxima of the composite segment and the threshold. Although the respiration rate may be determined from the local maxima of the composite segment and the threshold in any suitable manner, in an embodiment the first local maxima that exceeds the threshold may be selected, or if no local maxima exceeds the threshold, the global local maxima may be selected. In some embodiments, the selection may be performed by first identifying all of the local maxima and then comparing each local maxima to the threshold and disregarding any local maxima that are less than the threshold. Of the remaining local maxima, the first local maxima may be selected. If no local maxima remain, then the global maxima of the identified local maxima may be selected. With respect to processed composite signal 1402 of FIG. 14, local maxima 1404 may be selected as the first local maxima that exceeds a threshold and may be used to determine respiration rate. Local maxima 1404 is also the global local maxima in signal 1402. Respiration rate may then be determined based on the lag index associated with the selected local maxima and a conversion factor to breaths per minute. For example, respiration rate may be calculated as follows:

$$\text{respiration rate} = \frac{1}{\text{Lag index of selected local maxima} * dt}$$

where dt is the time interval between samples of the signal used to generate the composite segment.

The foregoing is merely illustrative of the principles of this disclosure and various modifications may be made by those skilled in the art without departing from the scope of this disclosure. The above described embodiments are presented for purposes of illustration and not of limitation. The present disclosure also can take many forms other than those explicitly described herein. Accordingly, it is emphasized that this disclosure is not limited to the explicitly disclosed methods, systems, and apparatuses, but is intended to include variations to and modifications thereof, which are within the spirit of the following claims.

What is claimed is:
1. A method comprising:
receiving a photoplethysmograph (PPG) signal;
processing, with processing equipment, plural windows of the PPG signal to generate plural respiration information signals;
generating, with the processing equipment, plural autocorrelation sequences based on the plural respiration information signals;
identifying first and second respiration peak segments of respective first and second autocorrelation sequences where the first and second autocorrelation sequences are derived from different data windows of said PPG signal;
determining, with the processing equipment, whether the first and second autocorrelation sequences include an undesired harmonic; and
calculating, with the processing equipment, respiration information based at least in part on the first and second autocorrelation sequences when it is determined that the autocorrelation sequences do not include an undesired harmonic.

2. The method of claim 1, further comprising calculating, with the processing equipment, a metric based on the autocorrelation sequences, wherein the metric is indicative of whether a particular pattern of peaks is present in the autocorrelation sequences and wherein the determination of whether the autocorrelation sequences includes an undesired harmonic is based on the metric.

3. The method of claim 2, wherein the particular pattern comprises a repeating sequence of small and large peaks.

4. The method of claim 1, further comprising:
identifying, with the processing equipment, a plurality of local maxima in the autocorrelation sequences;
calculating, with the processing equipment, a plurality of amplitudes associated with the plurality of local maxima; and
comparing, with the processing equipment, the plurality of amplitudes, wherein determining whether the autocorrelation sequences includes an undesired harmonic is based on the comparison of the plurality of amplitudes.

5. The method of claim 4, wherein the plurality of amplitudes comprises a sequence of amplitudes, and wherein comparing the plurality of amplitudes comprises determining whether subsequent amplitudes in the sequence are greater than the multiplication of the previous amplitudes in the sequence and a coefficient.

6. The method of claim 1, wherein determining whether the autocorrelation sequence includes an undesired harmonic is based on a threshold, the method further comprising modifying the threshold based on whether a previous autocorrelation sequence was determined to include an undesired harmonic.

7. The method of claim 1, further comprising not using an autocorrelation sequence in the calculation of the respiration information when it is determined that the autocorrelation sequence includes an undesired harmonic.

8. The method of claim 1, wherein calculating the respiration information based at least in part on autocorrelation sequences comprises:
identifying a respiration peaks of the autocorrelation sequences;
generating a composite peak based on a respiration peak and at least one previous respiration peak; and
calculating respiration information based at least in part on the composite peak.

9. The method of claim 8, wherein calculating the respiration information based at least in part on the composite peak comprises:
identifying a local maxima of the composite peak that exceeds a threshold; and
calculating the respiration information based at least in part on a lag index associated with the local maxima.

10. The method of claim 1, wherein the respiration information comprises respiration rate.

11. A system comprising:
an input for receiving a photoplethysmograph (PPG) signal; and
processing equipment configured for:
receiving a photoplethysmograph (PPG) signal;
processing plural windows of the PPG signal to generate to generate plural respiration information signals;
generating, with the processing equipment, plural autocorrelation sequences based on the plural respiration information signals;
identifying first and second respiration peak segments of respective first and second autocorrelation sequences where the first and second autocorrelation sequences are derived from different data windows of said PPG signal;
determining, with the processing equipment, whether the first and second autocorrelation sequences include an undesired harmonic; and
calculating, with the processing equipment, respiration information based at least in part on the first and second autocorrelation sequences when it is determined that the autocorrelation sequences do not include an undesired harmonic.

12. The system of claim 11, wherein the processing equipment is further configured for calculating a metric based on the autocorrelation sequences, wherein the metric is indicative of whether a particular pattern of peaks is present in the autocorrelation sequences and wherein the determination of whether the autocorrelation sequences includes an undesired harmonic is based on the metric.

13. The system of claim 12, wherein the particular pattern comprises a repeating sequence of small and large peaks.

14. The method of claim 11, wherein the processing equipment is further configured for:
identifying a plurality of local maxima in the autocorrelation sequences;
calculating a plurality of amplitudes associated with the plurality of local maxima; and
comparing the plurality of amplitudes, wherein determining whether the autocorrelation sequences include an undesired harmonic is based on the comparison of the plurality of amplitudes.

15. The system of claim 14, wherein the plurality of amplitudes comprises a sequence of amplitudes, and wherein comparing the plurality of amplitudes comprises determining whether subsequent amplitudes in the sequence are greater than the multiplication of the previous amplitudes in the sequence and a coefficient.

16. The system of claim 11, wherein determining whether the autocorrelation sequences include an undesired harmonic is based on a threshold, and wherein the processing equipment is further configured for modifying the threshold based on whether a previous autocorrelation sequence was determined to include an undesired harmonic.

17. The system of claim 11, wherein the processing equipment is further configured for not using the autocorrelation sequences in the calculation of the respiration information when it is determined that an autocorrelation sequence includes an undesired harmonic.

18. The system of claim 11, wherein the respiration information based at least in part on the autocorrelation sequences comprises:
identifying plural respiration peaks of the autocorrelation sequence;
generating a composite peak based on a respiration peak and at least one previous respiration peak; and
calculating respiration information based at least in part on the composite peak.

19. The system of claim 18, wherein calculating the respiration information based at least in part on the composite peak comprises:
identifying a local maxima of the composite peak that exceeds a threshold; and
calculating the respiration information based at least in part on a lag index associated with the local maxima.

20. The system of claim 11, wherein the respiration information comprises respiration rate.

* * * * *